US005717095A

United States Patent [19]

Arimilli et al.

[11] Patent Number: 5,717,095
[45] Date of Patent: Feb. 10, 1998

[54] NUCLEOTIDE ANALOGS

[75] Inventors: Murty N. Arimilli, Fremont; Robert J. Jones, Millbrae; Ernest J. Prisbe, Los Altos, all of Calif.

[73] Assignee: Gilead Sciences, Inc., Foster City, Calif.

[21] Appl. No.: 774,240

[22] Filed: Dec. 27, 1996

[51] Int. Cl.$^6$ .................................................. C07F 9/6574
[52] U.S. Cl. ........................................................... 544/243
[58] Field of Search .................................................. 544/243

[56] References Cited

U.S. PATENT DOCUMENTS

| | | | |
|---|---|---|---|
| 4,590,269 | 5/1986 | Prisbe et al. | 544/276 |
| 4,670,424 | 6/1987 | MacCoss et al. | 514/81 |
| 4,968,788 | 11/1990 | Farquhar | 536/27 |
| 5,142,051 | 8/1992 | Holy et al. | 544/244 |
| 5,247,085 | 9/1993 | Harnden et al. | |

FOREIGN PATENT DOCUMENTS

| | | |
|---|---|---|
| 0 269 947 A1 | 6/1988 | European Pat. Off. |
| 0 343 133 | 11/1989 | European Pat. Off. |
| 0 398 231 A2 | 11/1990 | European Pat. Off. |
| 0 405 748 | 1/1991 | European Pat. Off. |
| 0 481 214 A1 | 4/1992 | European Pat. Off. |
| WO 88/05438 | 7/1988 | WIPO. |
| WO 91/19721 | 12/1991 | WIPO. |
| WO 95/07919 | 3/1995 | WIPO. |
| WO 95/07920 | 3/1995 | WIPO. |

OTHER PUBLICATIONS

Andrei et al., "Comparative Activity of Selected Anitiviral Compounds against Clinical Isolates of Human Cytomegalovirus," Eur J Clin Microbiol Infect Dis 10(12):1026–1033 (1991).

Beres, "Synthesis and Antitumor and Antiviral Properties of 5–Halo–and 5–(Trifluoromethyl)–2'–deoxyuridine 3', 5'–Cyclic Monophosphates and Neutral Triesters," J Med Chem 29:1243–1249 (1986).

Bruice et al., "Hydrolysis of a Phosphate Diester by Simultaneous Carboxylate and Carboxyl Group Participation in a Rigid System with Kinetically Unfavorable Rotamers Frozen Out," J Am Chem Soc 117:3639–3640 (1995).

Engel, R., "Phosphonates as Analogues of Natural Phosphates," Chem Rev 77(3):349–367 (1977).

Freed et al., "Evidence for Acyloxymethyl Esters of Pyrimidine 5'–Deoxyribonucleotides as Extracellular Sources of Active 5'–Deoxyribonucleotides in Cultured Cells," Biochem Pharm 38:3193–3198 (1989).

Ho et al., "Intracellular Metabolism of the Antiherpes Agent (S)–1–[3–Hyroxy–2–(phosphonylmethoxy)propyl]cytosine," Mol Pharm 41:197–202 (1992).

Jones et al., "Minireview: nucleotide prodrugs," Antiviral Res 27:1–17 (1995).

Nielsen et al., "Evaluation of Glycolamide Estes and Various Other Esters of Aspirin as True Aspirin Produgs," J Med Chem 32:727–734 (1989).

Smee et al., "Potent Anti–Murine Cytomegalovirus Activity and Reduced Nephrotoxicity of Ganciclovir Cyclic Phosphonate," Antimicro Ag & Chemo 40(8):1964–1966 (Aug. 1996).

Primary Examiner—Michael G. Ambrose
Attorney, Agent, or Firm—Daryl D. Muenchau

[57] ABSTRACT

A cyclic nucleotide phosphonate ester characterized by the presence of an n-butyl salicylate ester group linked to the phosphorus atom of cHPMPC is disclosed. The analog comprises an ester bond that is hydrolyzed in vivo to yield a corresponding phosphonate nucleotide analog.

1 Claim, No Drawings

NUCLEOTIDE ANALOGS

CROSS REFERENCE TO RELATED APPLICATION

This application is a continuation of provisional application Ser. No. 60/009,372 filed Dec. 29, 1995, pending. Reference is made to related patent applications: U.S. application Ser. No. 08/123,483, now U.S. Pat. No. 5,656,745, 08/597,005, now U.S. Pat. No. 5,591,851, U.S. application Ser. No. 08/612,889, pending, U.S. application Ser. No. 08/581,147, pending and U.S. application Ser. No. 08/774,830, pending.

BACKGROUND OF THE INVENTION

The present invention relates to nucleotide analog esters, their pharmaceutically acceptable acid addition salts, processes for their production, and to their use.

Compounds related to the nucleotide analogs of the present invention may be found in: U.S. Pat. No. 5,043,339, 5,108,994 and 5,166,198; EP 206 459; EP 253 412; EP 269 947; EP 270 885; EP 319 228; EP 343 133; EP 398 231; EP 404 296; EP 465 297; EP 468 119; EP 468 866; EP 479 640; EP 481 214; EP 494 370; EP 531 597; PCT/GB91/01171; PCT/US92/01020; PCT/US92/05208; WO 91/19721; Bronson et al., *Bioorg Medicinal Chem Lett* (1992) 2:685–690; Bronson et al., *J Med Chem*, (1989) 32:1457–1463; Bronson et al., *Nucleotide Analogs as Antiviral Agents*, ACS Symposium Series 401, J. C. Martin, Ed., p. 72–87, American Chemical Society, Washington, D.C. (1989); Colla, et al., *J Med Chem* (1983) 26:602–604; Curley, et al., *Antiviral Res* (1990) 14:345–356; De Clercq, et al., *Nature*, (1986) 323:464–467; Farrow, et al., *J Med Chem* (1990) 33:1400–1406; Farquhar, et al., *J. Pharm Sci* (1983) 72:324–325; Freed, et al., *Biochem Pharmacol* (1989) 19:3193–3198; Freeman, et al., *J Med Chem* (1992) 35:3192–3196; Gabrielsen, B., et al., *Antiviral Res Suppl I* (1992) 7:149; Gumport, et al., *Proc Natl Acad Sci* (1971) 2559–2563; Juodka, et al., *Coll Czech Chem Commun* (1974) 39:963–968; Kim, et al., *Bioorg Medicinal Chem Lett* (1992) 2:367–370; Kim, et al., *Tet Lett* (1992) 33:25–28; Kim, et al., *J Med Chem* (1990) 35:1207–1213; Kumar, et al., *J Med Chem* (1990) 33:2368–2375; McGuigan, et al., *Antiviral Chem Chemother* (1993) 4:97–101; McGuigan, et al., *Antiviral Res* (1991) 15:255–263; Rosenberg, et al., *Coll Czech Chem Commun* (1988) 53:2753–2777; Rosenberg, et al., *Coll Czech Chem Commun* (1988) 52:2792–2800; Rosenberg, et al., *Coll Czech Chem Commun* (1988) 52:2801–2808; Starrett, et al., *Antiviral Res* (1992) 19:267–273; Yu, et al., *J Med Chem* (1992) 35:2958–2969; Wolff-Kugel, et al., *Tet Lett* (1991) 32:6341–6344.

A characteristic of nucleotide analogs or nucleotides having a phosphonate or a phosphate group is the presence of one or two negative charges associated with the phosphorus group at physiologic pH. Workers believe the charge associated with moieties such as phosphate or phosphonate groups generally limit oral bioavailability by limiting passive diffusion through the intestine membrane (Liebman, et al., *J. Biol. Chem.*, (1955) 216:823–830; Roll, et al., *J Biol Chem*, (1956) 220:439–444; Srivastava, et al., *Bioorg Chem* (1984) 12:118–129; Palu, et al., *Antiviral Res* (1991) 16:115–119; Sastry, et al., *Mol Pharmacol* (1992) 41:441–445). Workers often administer these compounds parenterally to obtain therapeutic serum or intracellular levels.

OBJECTS OF THE INVENTION

A principal object of the invention is to provide phosphonate esters of cyclic nucleotide analogs. These compounds can have improved pharmacokinetic or pharmacodynamic properties compared to the parent nucleotide analog that lacks the ester moiety. The nucleotide phosphonate esters (hereafter "NPEs") usually have increased oral bioavailability in humans and animals.

Another object is to provide NPEs with reduced toxicity and/or increased potency compared to the parent compound lacking the ester moiety. The invention provides NPEs that increase the therapeutic window for the parent nucleotide phosphonate by supplying it in a form that is less toxic in vivo while substantially retaining the parent nucleotide phosphonate antiviral activity.

Another object is to provide NPEs that deesterify while permitting subsequent biochemical or enzymatic conversion of the cyclic nucleotide analog to a desired ring opened derivative.

Other objects are to provide intermediates in the synthesis of the NPEs and to provide improved methods for NPE synthesis.

SUMMARY OF THE INVENTION

In a principal embodiment, nucleotide analogs comprising a phosphonate radical and a hydrolyzable ester linkage at the phosphonate phosphorus atom are objects of this invention. The NPEs hydrolyze in vivo to the corresponding nucleotide phosphonate and are thus precursors of the corresponding nucleotide phosphonate.

Principal invention embodiments are NPEs of formula (1) or a salt, solvate or racemate thereof

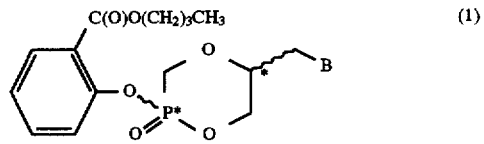
(1)

where B is a protected or unprotected cytosin-1-yl.

Atoms designated with (*) mean that the designated atom has constituents that are in the (R), (S) or (RS) configuration.

Invention embodiments include stereochemically enriched or resolved or substantially resolved NPEs and the carbon or the phosphorus atom chiral center * is as the (R) or (S) enantiomer.

Other embodiments include methods comprising orally administering to a subject an antivirally effective dose of an invention NPE.

Other embodiments include methods to prepare the invention stereochemically enriched NPEs at the phosphorus atom chiral center *.

Embodiments of the NPEs and their intermediates of the instant invention include the corresponding salts, which may be base salts of the phosphonic acid moiety, an acid addition salt of the base, their zwitterionic forms, their unionized forms, and/or any organic or aqueous solvate. Salts will typically be suitable for pharmaceutical or veterinary purposes, but also include salts that are useful for other purposes, e.g., NPE synthesis. Pharmaceutically acceptable non-toxic salts of these compounds may include those derived by combination of appropriate cations such as alkali and alkaline earth metal ions or ammonium and quaternary amino ions with the acid anion moiety of the phosphonic acid group. NPEs also include acid addition salts of certain organic and inorganic acids that result from reaction with basic centers of the purine, specifically guanine, or pyrimidine base.

The compounds of the present invention can comprise positional isomers or diastereomeric mixtures that may exist for certain compounds as well as the individual positional isomers which are all within the scope of the present invention. Compounds of formula (1) can be in the R, S or RS configuration at the chiral carbon, designated * herein. While one can separate the diastereomeric mixtures into their individual isomers through well-known techniques such as, for example, the separation of diastereomeric salts formed with optically active adjuncts, e.g., acids or bases followed by conversion back to the optically active substrates; in most instances, for compounds of the present invention, one can synthesize the preferred optical isomer by means of stereospecific reactions, beginning with the appropriate stereoisomer of the desired starting material.

NPE embodiments include NPEs labeled with a detectable tag such as a radioisotope (including $^{32}P$, $^{35}S$, $^{14}C$, $^{3}H$, $^{125}I$), a fluorescent moiety, an enzyme (including peroxidase, phosphatase) or the like.

Embodiments also include immunogens for raising antibodies that are capable of binding to the invention NPEs and/or their dihydroxy phosphonate hydrolysis products.

DETAILED DESCRIPTION OF THE INVENTION

As used herein, alkyl means linear, branched or cyclic saturated hydrocarbon moieties and includes all positional isomers, e.g., methyl, ethyl, propyl, isopropyl, butyl, sec-butyl, t-butyl, pentyl, isopentyl, neopentyl, n-hexyl, 1-methylpentyl, 2-methylpentyl, 1-ethylbutyl, 2-ethylbutyl, 3-ethylbutyl, cyclohexyl, n-heptyl, n-octyl, 2-ethylhexyl, n-nonyl, n-decyl and the like, unless the disclosure or context specifies otherwise. Alkyl, when used, e.g., to define the scope of formula (1) compounds can comprise about 5-20 carbon atoms or can comprise about 6-16 or about 6-12 carbon atoms. Halogen means F (fluorine), Cl (chlorine), Br (bromine) and I (iodine).

Substantially resolved means a compound enriched for a particular chiral species. A substantially resolved compound, such as a NPE substantially resolved at the chiral phosphorus atom, will often consist of at least about 65% or at least about 80% or at least about 90% of the (R) or (S) isomer. A resolved compound, such as a formula (1) NPE resolved at a chiral carbon atom means that the compound exists as 100% of a given configuration at the chiral atom, within the detection limits of conventional measurements.

Racemate or racemic mixture means any mixture containing 2 or more optical isomers of a given compound. For example, a formula (1) NPE racemate containing two positional or stereochemical isomers linked to or at the phosphorus atom may contain exactly 50% of each isomer or it may contain any amount above 50% and below 100% of a particular isomer.

Embodiments of formula (1) include NPEs stereochemically resolved or enriched as the (S) or (R) enantiomer at the carbon atom chiral center *. Embodiments of formula (1) include NPEs stereochemically resolved or enriched as the (S) or (R) enantiomer at the phosphorus atom chiral center *. NPEs enriched at the phosphorus atom chiral center *, consists of 55% to about 99.9% of the (S) or (R) enantiomer.

The formula (1) NPEs undergo a multistep chemical alteration that results in the biochemical or enzymatic formation of linear nucleotide phosphonate derivatives. For example, the NPEs of cHPMPC (1-[((S)-2-hydroxy-2-oxo-1,4,2-dioxaphosphorinan-5-yl)methyl]cytosine; cyclic HPMPC; formula (3) below) are converted to the ring opened form, (S)-HPMPC (formula (4) below) as shown. $R^x$ is the residue of a formula (1) NPE ester moiety in the formula (2) structure. The inventors believe that the final step, conversion of (3) to (4), is an intracellular event.

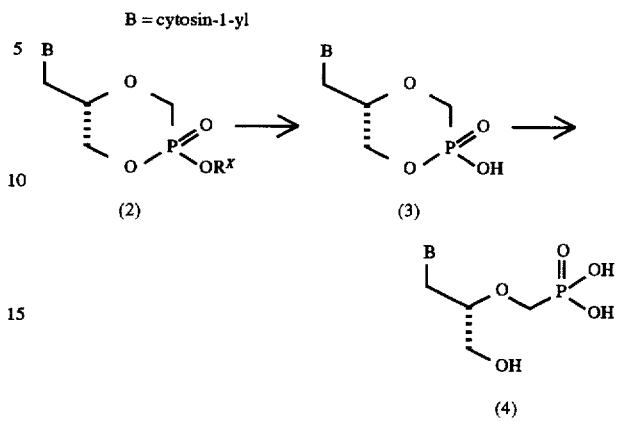

B includes both protected and unprotected forms of cytosine. Protecting groups for exocyclic amines and other groups are known (T. W. Greene et al., eds., *Protective Groups in Organic Synthesis* (1991), Wiley, 2nd ed.) and include N-benzoyl, isobutyryl, 4,4'-dimethoxytrityl (DMT) and the like. The selection of a protecting group will be apparent to the ordinary artisan and will depend on the nature of the labile group and the chemistry that the protecting group may encounter, e.g., acidic, basic, oxidative, reductive or other conditions.

One can select an NIPE based on the substrate specificity of esterases and/or carboxypeptidases one expects to find within cells where ester hydrolysis is desired. If the specificity of these enzymes is unknown, one determines the desired substrate specificity by screening a plurality of nucleotide phosphonate esters. This will be apparent from assay either of the generation of free phosphonate or of antiviral activity. One selects compounds that are (i) not hydrolyzed or hydrolyzed comparatively slowly in the upper gut, (ii) gut and cell permeable and (iii) hydrolyzed in the cell cytoplasm and/or systemic circulation. The artisan uses screens with cells from particular tissues to identify precursors that are released in organs susceptible to a target viral infection, e.g. in the case of liver, precursor drugs that the liver hydrolyzes. One treats other infections, e.g., CMV or HIV, with a precursor that the infected subject preferably hydrolyzes at substantially the same rate and to substantially the same degree in all or most tissues, with no one tissue preferentially hydrolyzing the nucleotide phosphonate esters to a significant degree.

The assays used can be those known in the art including intestinal lumen stability, cell permeation, liver homogenate stability and plasma stability assays. One uses these assays to determine the bioavailability characteristics of particular active nucleotide phosphonate esters according to routinely used methods.

The hydrolysis products of the NPEs have activity against viruses, malignant cells and/or parasitic protozoans. For example, 9-(3-hydroxy-2-phosphonylmethoxypropyl (HPMP) and analogs of purine (adenine (A), guanine (G), 2,6-diaminopurine (DAP), 2-monoaminopurine (MAP), hypoxanthine (Hx) and pyrimidine (cytosine (C), uracil (U), thymine (T) were evaluated for antiviral properties. (S)-HPMPA, (S)-cyclic HPMPA, (S)-HPMPC, (S)-HPMPG and (S)-HPMPDAP were active against herpes simplex virus, type 1 or 2 (HSV-1 and -2). (S)-HPMPA and (S)-cyclic HPMPA were active against varicella zoster virus (VZV), (S)-HPMPC was active against human cytomegalovirus (HCMV) in both humans and animals. (S)-HPMPA and (S)-cyclic HPMPA were shown to be active against adenovirus and vaccinia virus.

(S)-HPMPA has potent and selective activity against a broad spectrum of DNA viruses, including HSV-1 and 2, VZV, thymidine kinase-deficient (TK⁻) mutants of herpes simplex virus, HCMV, phocid herpesvirus type 1 (seal herpesvirus, SeHV), simian herpesvirus type 1 (SHV-1), or pseudorabies virus or Aujeszky's disease virus), bovid herpesvirus type 1 (infectious bovine rhinotracheitis virus, BHV-1), equid herpesvirus type 1 (equine abortion virus, EHV-1), African swine fever (ASF) virus, vaccinia virus; and human adenoviruses, and retroviruses such as murine sarcoma virus (MSV). The literature also reports that in mice and rabbits in vivo, the compound is effective against both local and systemic infections with herpes simplex virus type 1, including herpetic keratitis caused by a TK⁻ mutant which is resistant to the classical antiherpes drugs (DeClercq, E., et al., *Antiviral Res* (1987) 8:261–272; DeClercq, E., et al., *Nature* (1986) 323:464–467; Gil-Fernandez, C., et al., *Antiviral Res* (1987) 7:151–160; Baba, M., et al., *Antimicrob Agents Chemother* (1987) 31:337–339).

Researchers have also evaluated phosphonylmethoxyalkylpurine analogs for their antitumor activity in murine tumor models. They found that HPMPA was active against intraperitoneal P388 leukemia.

As indicated above, the compounds of the invention are useful for treatment of microbial infections, for treatment of tumors or for other indications described below. Microbial infections include infection by viruses, parasites, yeasts and fungi. Exemplary viral infections that may be treated include infections mediated by DNA or RNA viruses including herpesviruses (CMV, HSV 1, HSV 2, EBV, varicella zoster virus, bovid herpesvirus type 1, equid herpesvirus type 1), papillomaviruses (HPV types 1–55), flaviviruses (including African swine fever virus and Japanese encephalitis virus), togaviruses (including Venezuelan equine encephalomyelitis virus), influenza viruses (types A–C), retroviruses (HIV 1, HIV 2, HTLV I, HTLV II, SIV, HBV, FeLV, FIV, MoMSV), adenoviruses (types 1–8), poxviruses (vaccinia virus), enteroviruses (polio virus type 1–3, hepatitis A virus), gastroenteritis viruses (Norwalk viruses, rotaviruses), hantaviruses (Hantaan virus), papovaviruses, rhinoviruses, parainfluinza virus types 1–4, rabies virus, and the like.

One determines the activity of individual nucleotide analogs and nucleotide phosphonate esters by routine assay of antiviral (or other antimicrobial) activity using enzyme inhibition assays, tissue culture assays, animal model assays and/or other acceptable assays.

Researchers believe that nucleotide phosphonates such as HPMPC exert antimicrobial activity, at least in part, by a two step enzyme-mediated conversion to a diphosphate, followed by incorporation of the diphosphorylated nucleotide analog into nucleic acids. Virus-mediated or microbe-mediated incorporation of the diphosphates into nucleic acid uses viral or other microbial DNA or RNA polymerases (bacterial, retroviral, etc).

One can use the NPEs (1) in tissue culture systems to eliminate or reduce viral spread or growth during the production of biopharmaceuticals or other products (such as proteins or vaccines), (2) to eliminate or reduce viral spread or growth in clinical samples (such as blood), and (3) to reduce or block growth of viruses in tissue culture without interfering with protein production.

One can treat parasitic protozoan infections using the NPEs. The term protozoa includes those members of the subphyla Sarcomastigophora and Sporozoa of the phylum Protozoa. More particularly, the term protozoa as used herein includes those genera of parasitic protozoa which are important to man because they either cause disease in man or in his domestic animals. These genera are for the most part found classified in the superclass Mastighphora of the subphylum Sarcomastigophora and the class Telosporea of the subphylum Sporozoa in the classification according to Baker (1969). Illustrative genera of these parasitic protozoa include Histomonas, Pneumocystis, Trypanosoma, Giardia, Trichomonas, Eimeria, Isopora, Leishmania, Entamoeba, Toxoplasma and Plasmodium. Parasitic protozoans include *Plasmodium falciparum, Plasmodium berghei, Plasmodium malariae, Plasmodium vivax, Leishmania braziliensis, Leishmania donovani, Trypanosoma cruzi, Trypanosoma brucei, Trypanosoma rhodesiense, Pneumocystis carinii, Entamoeba histolytica, Trichomonas vaginalis* and the like (de Vries, E., et al., *Mol Biochem Parasitol* (1991) 47:43–50). NPEs of the invention and/or their corresponding nucleotide analogs can also be used to treat yeast or fungal infections caused by *Candida glabrata, Candida tropicalis, Candida albicans,* and other Candida species Cryptococcus species including *Cryptococcus neoformans,* Blastomyces species including *Blastomyces dermatidis,* Torulopsis species including *Torulopsis glabrata,* Coccidioides species including *Coccidioides immitis,* Aspergillus species and the like.

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

One can administer the active ingredients alone, but it is preferable to present them as pharmaceutical formulations. The formulations, both for veterinary and for human use, of the present invention comprise at least one active ingredient, as above defined, together with one or more acceptable carriers therefor and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. One can conveniently prepare the formulations in unit dosage form which using any of the methods known in the art of pharmacy. Such methods include the step of bringing into association the active ingredient with the carrier which constitutes one or more accessory ingredients. In general, one prepares the formulations by uniformly and intimately bringing into association the active ingredient with liquid carriers or finely divided solid carriers or both, and then, if necessary, shaping the product.

One can prepare the formulations of the present invention suitable for oral administration as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. One can also prepare the active ingredient as a bolus, electuary or paste.

One can make a tablet by compression or molding, optionally with one or more accessory ingredients. One prepares compressed tablets by compressing in a suitable machine the active ingredient in a free-flowing form such as a powder or granules, optionally mixed with a binder, lubricant, inert diluent, preservative, surface active or dispersing agent. One can make moulded tablets by molding in a suitable machine a mixture of the powdered compound moistened with an inert liquid diluent. One can optionally coat or score the tablets and formulate them to provide a slow or controlled release of the active ingredient.

One can apply, for infections of the eye or other external tissues e.g. mouth and skin, the formulations as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. One can employ an ointment formulation with the active ingredients in either a paraffinic or a water-miscible ointment base. Alternatively, one can formulate the active ingredients in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the present invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents such as pentamidine for treatment of pneumocystis pneumonia.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

The present invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods. Controlled release formulations may be employed for the treatment or prophylaxis of various microbial infections particularly human bacterial, human parasitic protozoan or human viral infections caused by microbial species including Plasmodium, Pneumocystis, herpesviruses (CMV, HSV 1, HSV 2, VZV, and the like), retroviruses, adenoviruses and the like. The controlled release formulations can be used to treat HIV infections and related conditions such as tuberculosis, malaria, pneumocystis pneumonia, CMV retinitis, AIDS, AIDS-related complex (ARC) and progressive generalized lymphadeopathy (PGL), and AIDS-related neurological conditions such as multiple sclerosis, and tropical spastic paraparesis. Other human retroviral infections that may be treated with the controlled release formulations according to the invention include Human T-cell Lymphotropic virus (HTLV)-I, -II and -IV, HIV-1 and HIV-2 infections.

The invention accordingly provides pharmaceutical formulations for use in the treatment or prophylaxis of the above-mentioned human or veterinary conditions and microbial infections.

For each of the above-indicated utilities and indications the amount required of an active ingredient (as above defined) will depend upon a number of factors including the severity of the condition to be treated and the identity of the recipient and will ultimately be at the discretion of the attendant physician or veterinarian. In general however, for each of these utilities and indications, a suitable, effective dose will be in the range 0.1 to 250 mg per kilogram bodyweight of recipient per dose (including active ingredient(s) in a range between 0.1 mg and 250 mg/Kg/dose in increments of 0.5 mg/Kg/dose such as 2.5 mg/Kg/dose, 3.0 mg/Kg/dose, 3.5 mg/Kg/dose, etc), preferably in the range 0.5 to 50 mg per kilogram body weight per dose and most preferably in the range 1 to 15 mg per kilogram body weight per dose; an optimum dose is about 3.0 mg per kilogram body weight per dose. (Unless otherwise indicated all weights of active ingredient are calculated as the parent compound of formula I: for salts thereof the figures would be increased proportionately). The desired dose is preferably presented as one dose or two sub-doses administered at appropriate intervals throughout a period of one to seven days. It is preferred to administer a dose once every 2, 3, 4, 5 or 6 days. The doses may be administered in unit dosage forms. The desired dose is may be presented as one, two, or three sub-doses administered at appropriate intervals throughout the one to seven day period. These sub-doses may be administered in unit dosage form, for example, containing 10 to 1000 mg, and or 100 to 500 mg of active ingredient per unit dosage form. The formulations should be desirably administered to achieve peak plasma concentrations of the active compound of from about 1 to about 100 μM, preferably about 2 to 50 μM, most preferably about 3 to about 30 μM.

Methods for administering esters of cHPMPC to humans is described in U.S. Ser. No. 08/193,341, which is incorporated herein by reference.

Formula (1) nucleotide phosphonate esters will generally (1) have a higher oral bioavailability than the corresponding uncyclized nucleotide analog (e.g., cHPMPC compared to HPMPC) and/or (2) will exibit reduced toxicity when compared with the same dose of the corresponding uncyclized nucleotide analog, and/or (3) will have greater efficacy when compared with the same dose of the corresponding uncyclized nucleotide analog.

The compounds of the invention may be employed in combination with other therapeutic agents for the treatment or prophylaxis of the infections or conditions indicated above. Examples of such further therapeutic agents include agents that are effective for the treatment or prophylaxis of viral, parasitic or bacterial infections or associated conditions or for treatment of tumors or related conditions include 3'-azido-3'-deoxythymidine (zidovudine, AZT), 2'-deoxy-3'-thiacytidine (3TC), 2',3'-dideoxy-2',3'-didehydroadenosine (D4A), 2'3'-dideoxy-2', 3'-didehydrothymidine (D4T), carbovir (carbocyclic 2'3'-dideoxy-2'3'-didehydroguanosine), 3'-azido-2'3'-dideoxyuridine, 5-fluorothymidine, (E)-5-(2-bromovinyl)-2'-deoxyuridine (BVDU), 2-chlorodeoxyadenosine, 2-deoxycoformycin, 5-fluorouracil, 5-fluorouridine, 5-fluoro-2'-deoxyuridine, 5-trifluoromethyl-2'-deoxyuridine, 6-azauridine, 5-fluoroorotic acid, methotrexate, triacetyluridine, 1-(2'-deoxy-2'-fluoro-1-β-arabinosyl)-5-iodocytidine (FIAC), tetrahydro-imidazo(4,5,1-jk)-(1,4)-benzodiazepin-2(1H)-thione (TIBO), 2'-nor-cyclicGMP, 6-methoxypurine arabinoside (ara-M), 6-methoxypurine arabinoside 2'-O-valerate, cytosine arabinoside (ara-C), 2'3'-dideoxynucleosides such as 2'3'-dideoxycytidine (ddC), 2'3'-dideoxyadenosine (ddA) and 2'3'-dideoxyinosine (ddI), acyclic nucleosides such as acyclovir, penciclovir, famciclovir, ganciclovir, HPMPC, PMEA, PMEG, PMPA, PMPDAP, FPMPA, HPMPA, HPMPDAP, (2R, 5R)-9-[tetrahydro-5-(phosphonomethoxy)-2-furanyl]adenine, (2R, 5R)-1-[tetrahydro-5-(phosphonomethoxy)-2-furanyl]thymine, other antivirals including ribavirin (adenine arabinoside), 2-thio-6-azauridine, tubercidin, aurintricarboxylic acid, 3-deazaneoplanocin, neoplanocin, rimantidine, adamantine, and foscarnet (trisodium phosphonoformate), antibacterial agents including bactericidal fluoroquinolones (ciprofloxacin, pefloxacin and the like), aminoglycoside bactericidal antibiotics (streptomycin, gentamicin, amicacin and the like) β-lactamase inhibitors (cephalosporins, penicillins and the like), other antibacterials including tetracycline, isoniazid, rifampin, cefoperazone, claithromycin and azithromycin, antiparasite or antifungal agents including pentamidine (1,5-bis(4'-aminophenoxy)pentane), 9-deazainosine, sulfamethoxazole, sulfadiazine, quinapyramine, quinine, fluconazole, ketoconazole, itraconazole, Amphotericin B, 5-fluorocytosine, clotrimazole, hexadecylphosphocholine and nystatin, renal excretion inhibitors such as probenicid, nucleoside transport inhibitors such as dipyridamole, dilazep and nitrobenzylthioinosine, immunomodulators such as FK506, cyclosporin A, thymosin α-1, cytokines including TNF and TGF-β, interferons including IFN-α, IFN-β and IFN-γ, interleukins including interleukin I, II, III, IV, V, VI, VII, VIII, X, XII, XIII macrophage/granulocyte colony stimulating factors including GM-CSF, G-CSF, M-CSF, cytokine antagonists including anti-TNF antibodies, anti-interleukin antibodies, soluble interleukin receptors, protein kinase C inhibitors and the like.

The compounds of this invention, or the biologically active substances produced from these compounds by hydrolysis in vivo, are used as immunogens to prepare antibodies capable of binding specifically to the compounds or their hydrolysis products. The immunogenic compositions therefore are useful as intermediates in the preparation of antibodies for use in diagnostic or quality control assays for the compounds or their hydrolysis products. The antibodies are useful for measuring the presence, absence or amounts of the compounds by any convenient homogenous or heterogenous procedure such as fluorescence polarization immunoassay, fluorescence immunoassay (using fluorescent labels such as fluorescein and the like), radioimmunoassay, enzyme immunoassay (using enzyme indicators such as alkaline phosphatase, horseradish peroxidase, glucose oxidase, urease and the like) and nephelometric inhibition assay by described methods (WO 92/22639, incorporated herein by reference). Such assays usually require a tracer (such as a fluorescent or radiolabeled labeled invention compound), an antibody and the sample to be analyzed containing the compound.

The immunogens of this invention contain the precursor or hydrolytic products in association with an immunogenic substance such as a protein or peptide. Immunogenic substances include adjuvants such as Freund's adjuvant, immunogenic proteins such as viral, bacterial, yeast, plant and animal polypeptides, in particular keyhole limpet hemocyanin, serum albumin, bovine thyroglobulin or soybean trypsin inhibitor, and immunogenic polysaccharides. Typically, the precursor or a compound having the structure of a precursor hydrolytic product is covalently conjugated to an immunogenic polypeptide or polysaccharide by the use of a polyfunctional (ordinarily bifunctional) cross-linking agent. Methods for the manufacture hapten immunogens are conventional per se, and any of the methods previously used for conjugating haptens to immunogenic polypeptides or the like are suitably employed here as well, taking into account the functional groups on the precursors or hydrolytic products which are available for cross-linking.

Typically the polypeptide is conjugated to a site on the heterocyclic base functionality of the compound or hydrolysis product rather than to a site on the alkyl or substituted-alkyl phosphonate moiety. In general, the site will be an amino group located on the purine or pyrimidine moiety of the nucleoside phosphonate, at the 5 position of pyrimidines (such as cytosine or uracil), at the 1 position of purines (such as adenosine or guanine) or, for compounds having a cyclic structure corresponding to a sugar or sugar analog and having a free hydroxyl group, through the hydroxyl group (usually at the 3' or 2' positions). Alternatively, the precursor compound is cross-linked through the phosphonate, typically by amidation or esterification of the phosphonate by the polypeptide itself or by a cross-linking functionality covalently bonded to the polypeptide.

The conjugates are prepared in conventional fashion. For example, N-hydroxysuccinimide, succinic anhydride or alkN=C=Nalk are useful in preparing the conjugates of this invention. The conjugates contain a precursor, its hydrolysis product, or both. Ordinarily, the conjugates will comprise the hydrolysis product, i.e., the biologically active drug. The conjugates are separated from starting materials and byproducts using chromatography or the like, and then are sterile filtered and vialed for storage.

Animals are typically immunized against the immunogenic conjugates or derivatives by combining 1 mg or 1 μg of conjugate (for rabbits or mice, respectively) with 3 volumes of Freund's complete adjuvant and injecting the solution intradermally at multiple sites. One month later the animals are boosted with ⅕ to ¹⁄₁₀ the original amount of conjugate in Freund's complete adjuvant (or other suitable adjuvant) by subcutaneous injection at multiple sites. 7 to 14 days later animals are bled and the serum is assayed for the desired antibody titer. Animals are boosted until the titer plateaus. Preferably, the animal is boosted with the conjugate in which the precursor or product is linked to a different protein, through a different cross-linking agent or both. Optionally, aggregating agents such as alum are used to enhance the immune response.

After immunization, monoclonal antibodies are prepared by recovering immune lymphoid cells (typically spleen cells or lymphocytes from lymph node tissue) from immunized animals and immortalizing the cells in conventional fashion, e.g., by fusion with myeloma cells or by Epstein-Barr virus transformation and screening for clones expressing the desired antibody. The hybridoma technique described originally be Kohler and Milstein, *Eur. J. Immunol.* (1976) 6:511 has been widely applied to produce hybrid cell lines that secrete high levels of monoclonal antibodies against many specific antigens.

It is possible to fuse cells of one species with another. However, it is preferably that the source of the immunized antibody producing cells and the myeloma be from the same species.

The hybrid cell lines are maintained in culture in vitro. The cell lines of this invention are selected or maintained in a hypoxanthine-aminopterin thymidine (HAT) medium. However, the established hybridoma cell line can be maintained on a variety of nutritionally adequate media. The secreted antibody is recovered from culture by conventional methods such as precipitation, ion exchange chromatography, affinity chromatography, or the like. The antibodies described herein are also recovered from hybridoma cell cultures by conventional methods for purification of IgG or IgM as the case may be that heretofore have been used to purify immunoglobulins from pooled plasma, e.g., ethanol or polyethylene glycol precipitation procedures. The purified antibodies are sterile filtered, and optionally are conjugated to a detectable marker such as an enzyme or spin label for use in diagnostic assays of test samples.

The antibodies of this invention are obtained from any animal species, but ordinarily are murine or rat. Once a monoclonal antibody having the desired specificity and affinity is obtained, other conventional modifications of the antibodies are within the scope of this invention. For example, the complementarity determining regions of an animal antibody, together with as much of the flamework domain as is needed, are substituted into an antibody of another animal species or class to produce a cross-class or cross-species chimeric antibody. Fragments or other amino acid sequence variants of monoclonal antibodies also are encompassed within the meaning of antibody as that term is used herein, for example, Fab, Fab' or (Fab')2 fragments, single chain antibodies, bi or polyspecific antibodies, and the like.

The antibodies of this invention are from any suitable class or isotype, e.g. IgG, IgM, IgA, IgD or IgE. They may or may not participate in complement binding or ADCC.

Typically, hybridomas which are capable of binding to the immunogen are screened for the ability to bind to the hapten itself in typical test samples (plasma, serum and the like) with the requisite degree of affinity. The desired affinity will depend upon the use intended for the antibody, but should be adequate to function in a conventional competitive-type ELISA or radioimmunoassays, or in conventional EMIT immunoassays.

The antibodies of this invention are used in such assays together with a labeled from of the precursor or its hydrolytic product. Alternatively, the antibody is labeled. Suitable labels are well-known and include radioisotopes, enzymes, stable free radicals, fluorophors, chemiluminescent moieties and other detectable groups heretofore employed to prepare covalent conjugates for use in assays. Methods for linking the labels to ligand amino groups, or amino acid side chains or termini of polypeptides, are known and are suitable for use herein. Other suitable linking methods will be apparent to the ordinary artisan.

The antibodies and labeled ligands herein optionally are assembled into kits for use in therapeutic drug monitoring or evaluation, or for process quality control, and used in the conventional manner.

cHPMPC and the cyclic analogs of other cHPMPs are prepared by a number of methods from the free hydroxy phosphonic acid. These methods include treatment with DCC in DMF, reaction with Vilsmeier's reagent (ClCH=N(CH$_3$)$_2$Cl, or methods of phosphate activation known per se. In one method for the preparation of a cHPMP from the corresponding phosphonate nucleotide analog, the phosphonate is (a) treated with ClCH=N(CH$_3$)$_2$Cl to yield the phosphonylchloridate and (b) optionally the phosphonylchoridate is reacted with a nucleophile (preferably at low temperature, e.g. lower than about −20° C.) such as an alcohol or amine to produce one of the intermediates described above. In a further step the product of steps (a) or (b) are subject to hydrolysis or protonolysis (typically acid protonolysis) respectively to yield the cHPMP (treatment of the product of step (a)) or its intermediate (treatment of the product of step (b)). Vilsmeier's reagent is advantageously produced in situ by combining SOCl$_2$, PCl$_5$, POCl$_3$, COCl$_2$ or the like with DMF. Advantageously, the product of step (a) is not purified or separated from the reaction mixture before being reacted with the nucleophile, a distinct economic advantage for this synthetic route. The compounds of structure (Ia) and (Va) are readily made from their uncyclized counterparts by the same methods, e.g. treatment with DCC in DMF.

Substituted and unsubstituted alkyl, aryl, heteroaryl, arylalkyl and heteroarylalkyl esters of cHPMPs typically are made by reacting the appropriate HPMP compound with SOCl$_2$/DMF to yield the activated phosphonylchloride (see Scheme 1), followed by treatment with the corresponding nucleophile (e.g. alkoxide, phenolate, amine, etc.) to yield the protected intermediate formamidine which is subsequently hydrolyzed to the target compound. Alternatively, esters can also be prepared as depicted in Scheme 2. The N-,O- protected intermediate phosphonate diester is obtained from the three building blocks by known methods. The N- and O- protecting groups are subsequently removed followed by treatment of the phosphonate diester 3 with NaH leading to cyclization yielding target compound 4. A third method for the synthesis of cHPMP esters entails alkylation of the cHPMP using common alkylating agents $R^{15}L$ (where L is a leaving group) such as alkyl halides, tosylates, diazoalkanes and the like (see Scheme 3). This method is particularly useful for preparing acyloxyalkyl esters by treatment of the cHPMP with the corresponding acyloxyalkylhalide.

In an exemplary method for the preparation of acyloxyalkyl esters of cHPMPs, as shown in more detail in Example 12, DCC and $R^{16}C(O)OCH_2Cl$ are reacted with the cyclic compound; but in contradistinction with prior methods the stoichiometric proportion of DCC: $R^{16}C(O)OCH_2Cl$, cyclic HPMP is 1-2:1-2:1. Use of such low proportions of reactants lessens side reactions with any exocyclic amino group of B and thereby greatly improves yields. $R^{16}$ is H or is $C_3$–$C_{12}$ alkyl which is unsubstituted or substituted by substituents independently selected from the group consisting of OH, O, N and halogen, $C_3$–$C_6$ aryl which is unsubstituted or substituted by substituents independently selected from the group consisting of OH, O, N and halogen or $C_3$–$C_9$ aryl-alkyl which is unsubstituted or substituted by substituents independently selected from the group consisting of OH, O, N and halogen.

Each of the following schemes exemplify HPMPC as the nucleotide analog. However, any B is employed in place of cytosine, provided that any exocyclic oxo or amino groups are protected as required. Also, step 3 of scheme 1 will be omitted when B contains no exocyclic amine.

Scheme 1

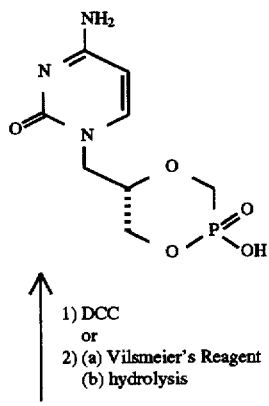

1) DCC
or
2) (a) Vilsmeier's Reagent
(b) hydrolysis 5,717,095
-continued
Scheme 1
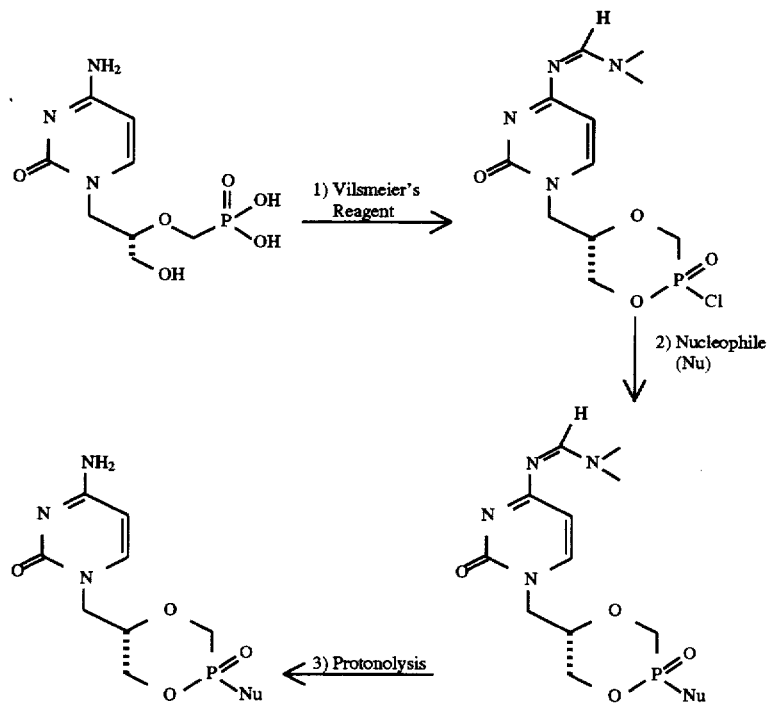
Scheme 2
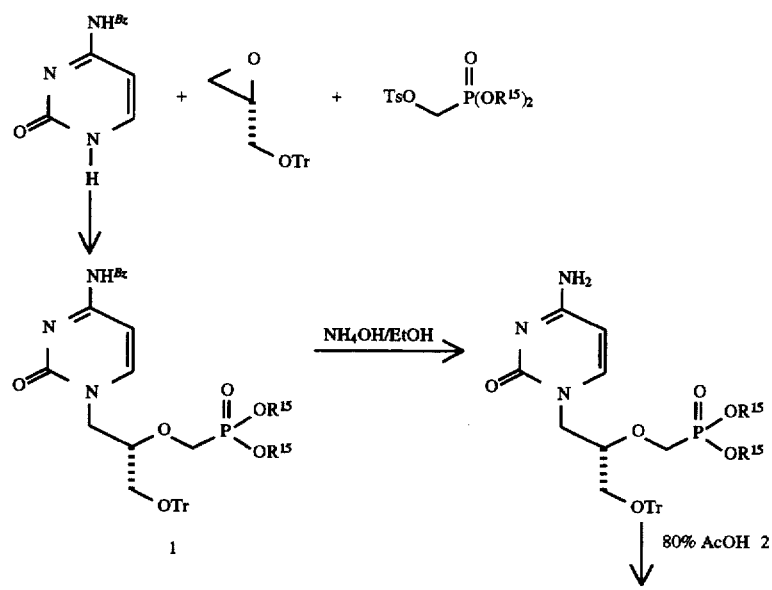

Scheme 2 (continued)

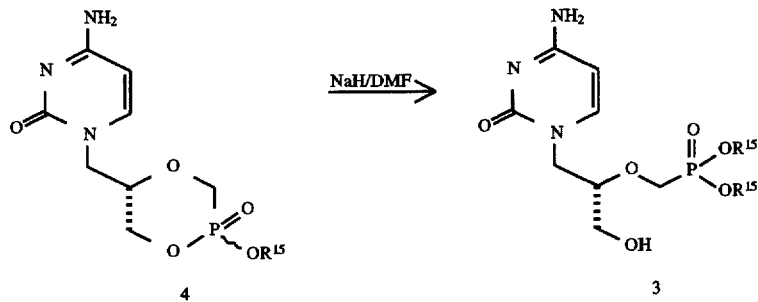

Scheme 3

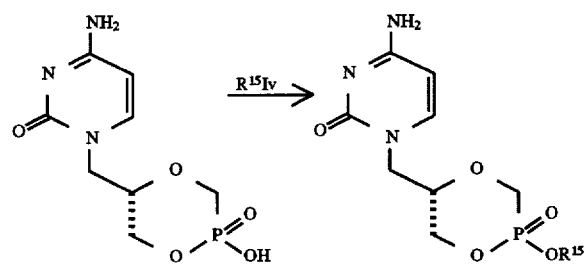

A third method for the synthesis of cyclic HPMP esters entails alkylation of the cyclic HPMP ester as shown in Scheme 3 using common alkylating agents $R^{15}Lv$ such as alkyl halides, tosylates, diazoalkanes and the like. This method is particularly useful for preparing acyloxyalkyl esters by treatment of the cyclic HPMP (cHPMP) with the corresponding acyloxyalkylhalide.

$R^{15}$ is defined as the following groups and species: H, alkyl (e.g., $C_{1-20}$ or $C_{4-12}$) which is unsubstituted or substituted by substituents independently selected from the group consisting of OH, O, N and halogen (F, Cl, Br, I), aryl (e.g., $C_{4-12}$ or $C_{3-20}$) which is unsubstituted or substituted by substituents independently selected from the group consisting of alkyl (e.g., $C_1$–$C_8$ or $C_1$–$C_{1-6}$), alkoxy (e.g., $C_1$–$C_8$ or $C_{1-6}$), haloalkyl (e.g., $C_1$–$C_8$ or $C_{1-6}$, 1 to 3 halogen atoms), cyano, nitro, OH, O, N and halogen, or $R^{15}$ is $C_{4-20}$ aryl-alkyl which is unsubstituted or substituted in the aryl moiety by substituents independently selected from the group consisting of $C_{1-6}$ alkyl, $C_{1-6}$ alkoxy, $C_{1-6}$ haloalkyl (1 to 3 halogen atoms), cyano, nitro, OH, O, N and halogen, or $R^{15}$ is $C_{3-24}$ 1-acyloxy-1-alkyl (e.g., $C_{1-8}$ alkyl), or $R^{15}$ is $C_{6-24}$ 1-acyloxy-1-aryl-1-alkyl (e.g., $C_{1-6}$ aryl, $C_{1-4}$ alkyl), or $R^{15}$ is $C_{3-24}$ 1-acyloxy-2-alkoxy-1-alkyl ($C_{1-8}$ alkyl), or $R^{15}$ is $C_{3-24}$ 1-acyloxy-2-haloalkyl ($C_{1-8}$ haloalkyl, 1 to 3 halogen atoms), or $R^{15}$ is phenyl, 2- or 3-pyrrolyl, 2- or 3-thienyl, 2- or 4-imidazolyl, 2-, 4- or 5-oxazolyl, 3- or 4-isoxazolyl, 2-, 4- or 5-thiazolyl, 3-, 4- or 5-isothiazolyl, 3- or 4-pyrazolyl, 2-, 3- or 4-pyridinyl, 2-, 4- or 5-pyrimidinyl, 2-, 3- or 4-alkoxyphenyl ($C_1$–$C_{12}$ alkyl including 2-, 3- and 4-methoxyphenyl or 2-, 3- or 4-ethoxyphenyl), 2-, 3-or 4-halophenyl (including 2-, 3- and 4-fluorophenyl), 2,3-, 2,4-, 2,5-, 2,6-, 3,4- or 3,5-dihalophenyl (including 2,4-difluorophenyl and 2,4-dichlorophenyl), 2-, 3- or 4-haloalkylphenyl (1 to 5 halogen atoms, $C_{1-12}$ alkyl including 2-, 3- and 4-trifluoromethylphenyl and 2-, 3- and 4-trichloromethylphenyl), 2-, 3- or 4-cyanophenyl, alkoxycarbo phenyl ($C_{1-12}$ alkyl including 2-, 3- and 4-n-butoxycarbophenyl, $-C_6H_4-C(O)-OC_4H_9$, and including 2-, 3- or 4-hexoxycarbophenyl, $-C_6H_4-C(O)-OC_6H_{13}$, $-C_6H_4-C(O)-OC_6H_{11}$) or 2,3-, 2,4-, 2,5-, 2,6-, 3,4- or 3,5-diethoxycarbophenyl, 1-, 2-, 3-, or 4-pyridinyl ($-C_5H_4N$), 2-, 3- or 4-nitrophenyl, 2-, 3- or 4-haloalkylbenzyl (1 to 5 halogen atoms, $C_1$–$C_{12}$ alkyl including 4-trifluoromethylbenzyl), alkylsalicylphenyl ($C_{1-4}$, $C_{3-10}$ or $C_{6-12}$ alkyl including 2-, 3- and 4-butylsalicylphenyl), 2-,3- or 4-acetylphenyl, 1,8-dihydroxy-naphthyl ($-O-C_{10}H_6-OH$ or $-O-C_{10}H_6-O-$), 2,2'-dihydroxybiphenyl ($-O-C_6H_4-C_6H_4-O-$; both oxygen atoms are linked to the phosphorus atom), alkoxy ethyl ($C_{1-6}$ alkyl including $-CH_2-CH_2-O-CH_3$ (methoxy ethyl) and phenoxymethyl), aryloxy ethyl ($C_{5-10}$ or $C_{6-9}$ aryl (including phenoxy ethyl) or $C_{5-10}$ or $C_{6-9}$ aryl substituted by OH, $NH_2$, halo, $C_{1-4}$ alkyl or $C_{1-4}$ alkyl substituted by OH or by 1 to 3 halo atoms], $-C_6H_4-CH_2-N(CH_3)_2$, N-ethylmorpholino $$\left( \underset{}{\diagdown} N \diagup \underset{}{\diagdown} \diagup O \right); \ -(CH_2)_2-N[(CH_2)_2(CH_2)_2]O),$$

adamantoyl oxymethyl, pivaloyloxy(methoxyethyl)methyl
$(-CH(CH_2CH_2OCH_3)-O-C(O)-C(CH_3)_3)$, $; -O-CH_2-O-C(O)-C_{10}H_{15})$, pivaloyloxymethyl $(-CH_2-O-C(O)-C(CH_3)_3)$, pivaloyloxy(methoxymethyl)-methyl $(-CH(CH_2OCH_3)-O-C(O)-C(CH_3)_3)$, pivaloyloxyisobutyl $(-CH(CH(CH_3)_2)-O-C(O)-C(CH_3)_3)$ isobutyryloxymethyl $(-CH_2-O-C(O)-CH_2-CH(CH_3)_2)$, cyclohexanoyl oxymethyl $(-CH_2-O-C(O)-C_6H_{11})$, phenyl $(-C_6H_5)$, benzyl $(-CH_2-C_6H_5)$, isopropyl, t-butyl, $-CH_2-CH_3$, $-(CH_2)_2-CH_3$, $-(CH_2)_3-CH_3$, $-(CH_2)_4-CH_3$, $-(CH_2)_5-CH_3$, $-Ch_2-CH_2F$, $-CH_2-CH_2Cl$, $-CH_2-CF_3$, $-CH_2-CCl_3$, $R^A$, $NHR^B$ or $N(R^B)_2$ wherein $R^A$ is $CH_2C(O)N(R^B)_2$, $CH_2C(O)OR^B$, $CH_2OC(O)R^B$, $CH(R^B)OC(O)R^B$, $CH_2C(R^B)_2CH_2OH$, $CH_2OR^B$, $NH-CH_2-C(O)O-CH_2CH_3$, $N(CH_3)-CH_2-C(O)O-CH_2CH_3$, $CH_2-O-C(O)-C_6H_5$, $CH_2-O-C(O)-C_{10}H_{15}$, $-CH_2-O-C(O)-CH_2CH_3$, $CH_2-O-C(O)-CH(CH_3)_2$, $CH_2-O-(O)-C(CH_3)_3$, $CH_2-O-C(O)-CH_2-C_6H_5$, wherein $R^B$ is $C_{1-20}$ alkyl which is unsubstituted or substituted by substituents independently selected from the group consisting of OH, O, N and halogen (1 to 5 halogen atoms), $C_{6-20}$ aryl which is unsubstituted or substituted by substituents independently selected from the group consisting of OH, O, N and halogen (1 to 5 halogen atoms) or $C_{7-20}$ aryl-alkyl which is unsubstituted or substituted by substituents independently selected from the group consisting of OH, O, N and halogen (1 to 5 halogen atoms), provided that for compounds of formulas $N(R^B)_2$, $CH_2C(O)N(R^B)_2$, $CH_2C(O)OR^B$, $CH_2OC(O)R^B$, $CH(R^B)OC(O)R^B$ and $CH_2C(R^B)_2CH_2OH$, the total number of carbon atoms present is less than 25 (usually the number of carbon atoms present is about 4 to about 14), or $R^{15}$ is 2,3-dihydro-6-hydroxyindene, sesamol, catechol monoester, —$CH_2$—$C(O)$—$N(R^C)_2$ (wherein each $R^C$ is the same or different and $R^C$ is H or $C_{1-4}$ or $C_{2-10}$ alkyl) —$CH_2$—$S(O)$ ($R^C$), —$CH_2$—$S(O)_2(R^C)$, —$CH_2$—$CH(OC(O)CH_2R^C)$, —$CH_2(OC(O)CH_2R^C)$, cholesteryl, a 5 or 6 carbon monosaccharide, disaccharide or oligosaccharide (3 to 9 monosaccharide residues), enolpyruvate (HOOC—C (=$CH_2$)O), glycerol, α-D-β-diglycerides (wherein the fatty acids composing glyceride lipids generally are naturally occurring saturated or unsaturated $C_{6-26}$, $C_{6-18}$ or $C_{6-10}$ fatty acids such as linoleic, lauric, myristic, palmitic, stearic, oleic, palmitoleic, linolenic and the like fatty acids), trimethoxybenzyl, triethoxybenzyl, 2-alkyl pyridinyl ($C_{1-4}$ alkyl),

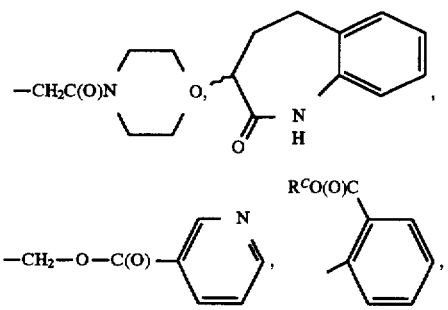

$C_3$—$C_6$ aryl (including phenyl, 2- and 3-pyrrolyl, 2- and 3-thienyl, 2- and 4-imidazolyl 2-, 4- and 5-oxazolyl, 3- and 4-isoxazolyl, 2-, 4- and 5-thiazolyl, 3-, 4- and 5-isothiazolyl, 3- and 4-pyrazolyl, 2-, 3- and 4-pyridinyl and 2-, 4- and 5-pyrimidinyl) substituted by 3, 4 or 5 halogen atoms or 1 or 2 atoms or groups selected from halogen, $C_{1-12}$ alkoxy (including methoxy, ethoxy, propyloxy, butyloxy, 2,3-, 2,4-, 2,5-, 2,6-, 3,4- and 3,5-dimethoxy and 2,3-, 2,4-, 2,5-, 2,6-, 3,4- and 3,5-diethoxy substituted phenyl), cyano, nitro, OH, $C_{1-12}$ haloalkyl (1 to 6 halogen atoms), $C_{1-12}$ alkyl (including methyl and ethyl), $C_{2-12}$ alkenyl or $C_{2-12}$ alkynyl; or $R^{15}$ is $C_{1-4}$ alkylene—$C_3$—$C_6$ aryl (including benzyl, —$CH_2CH_2$—$C_6H_5$, —$CH_2$—pyrrolyl, —$CH_2$—thienyl, —$CH_2$—imidazolyl, —$CH_2$—oxazolyl, —$CH_2$—isoxazolyl, —$CH_2$—thiazolyl, —$CH_2$—isothiazolyl, —$CH_2$—pyrazolyl, —$CH_2$—pyridinyl and —$CH_2$—pyrimidinyl) substituted in the aryl moiety by 3 to 5 halogen atoms or 1 to 2 atoms or groups selected from halogen, $C_{1-12}$ alkoxy (including methoxy and ethoxy), cyano, nitro, OH, $C_{1-12}$ haloalkyl (1 to 6 halogen atoms; including —$CH_2$— $CCl_3$), $C_{1-12}$ alkyl (including methyl and ethyl), $C_{2-12}$ alkenyl or $C_{2-12}$ alkynyl. Methods for linking cholesteryl, saccharide and other moieties to reactive groups have been described (Hadfield *Adv. Pharmacol. Chemother.* (1984) 20:21; Gouyette *Tet. Lett.* (1989) 30:6019; Ksander *J. Med. Chem.* (1994) 37:1823).

Other compounds are used as intermediates in the synthesis of mixed amidate-ester nucleotide analog amidates, or in some cases, as drugs per se. Other ester compounds have the formulas $(R^{15}O)_2P(O)$—$Z^1$—B where $Z^1$ is defined to mean the substructure in the following representative structures; $(R^{15}O)_2$—$P(O)$—$CH_2$—$O$—$CH_2$—$CH_2$—B, $(R^{15}O)_2$—$P(O)$—$CH_2$—$O$—$C\#H(CH_2OH)$—$CH_2$—B, $(R^{15}O)_2$—$P(O)$—$CH_2$—$O$—$C\#H(CH_3)$—$CH_2$—B, $(R^{15}O)_2$—$P(O)$—$CH_2$—$O$—$C\#H(CH_2F)$—$CH_2$—B, $(R^{15}O)_2$—$P(O)$—$CH_2$—$O$—$C\#H(CH=CH_2)$—$CH_2$—B, $(R^{15}O)_2$—$P(O)$—$CH_2$—$O$—$C\#H(CH_2N_3)$—$CH_2$—B and

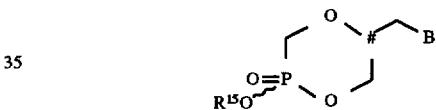

where C# and # includes linked substituents in the (R), (S) or (RS) configurations and where each $R^{15}$ is the same or different and each $R^{15}$ is independently chosen.

Table 2 lists a group of exemplary bis esters of compounds having the structure $(OR^{15})_2P(O)$—Z—B.

TABLE 2

| $OR^{15}*$ | | $=P(O)-Z-B**$ | |
|---|---|---|---|
| 1 | $-O-C_6H_4F$ | 1 | $=P(O)-CH_2-O-CH_2-CH_2-B$ |
| 2 | $-O-C_6H_3F_2$ | 2 | $=P(O)-CH_2-O-C\#H(CH_2-OH)-CH_2-B$ |
| 3 | $-O-C_6H_4-OCH_3$ | 3 | $=P(O)-CH_2-O-C\#H(CH_3)-CH_2-B$ |
| 4 | $-O-C_6H_3-(OCH_3)_2$ | 4 | $=P(O)-CH_2-O-C\#H(CH_2F)-CH_2-B$ |
| 5 | $-O-C_6H_4-OC_2H_5$ | 5 | $=P(O)-CH_2-O-C\#H(CH-CH_2)-CH_2-B$ |
| 6 | $-O-C_6H_3-(OC_2H_5)_2$ | 6 | $=P(O)-CH_2-O-C\#H(CH_2N_3)-CH_2-B$ |
| 7 | $-O-CH_2-C_6H_4F$ | | |
| 8 | $-O-C_6H_4-(C(O)-O-C_4H_9)_2$ | 7*** | |

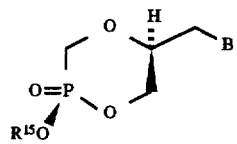

TABLE 2-continued

| | | | |
|---|---|---|---|
| 9 | $-O-C_6H_4-C(O)-O-C_2H_5$ | 8 | (structure: cyclic phosphonate with O=P, $R^{15}O$, and CH$_2$-B side chain) |
| 10 | $-O-CH_2-O-C(CH_3)_3$ | | |
| 11 | $-O-C_6H_5\text{-}o\text{-}C(O)OCH_2CH(CH_2CH_3)CH_2CH_2CH_2CH_3$ | | |
| 12 | $-O-C_6H_5\text{-}o\text{-}C(O)OCH_2CH_2CH_2CH_2CH_2CH_2CH_3$ | | |
| 13 | $-O-C_6H_5\text{-}o\text{-}C(O)OCH_2CH_2CH_2CH_2CH_3$ | | |
| 14 | $-O-C_6H_5\text{-}o\text{-}C(O)OCH_2CH_2CH_2CH_3$ | | |
| 15 | $-O-C_6H_5\text{-}o\text{-}C(O)OCH_2CH_2CH_3$ | | |
| 16 | $-O-C_6H_5\text{-}o\text{-}C(O)OCH_2CH_2C_6H_5$ | | |

B

| 1 | adenin-9-yl |
|---|---|
| 2 | guanin-9-yl |
| 3 | cytosin-1-yl |
| 4 | 2,6-diaminopurin-9-yl |
| 5 | 2-aminopurin-9-yl |
| 6 | 5-methylcytosin-1-yl |
| 7 | 5-fluorocytosin-1-yl |

*Monosubstituted phenyl and benzyl compounds (i.e., $R^{15}$ numbers 1, 3, 5, etc) include 2-, 3- and 4-substituted compounds and disubstituted phenyl compounds (i.e., $R^{15}$ numbers 2, 4, 6, etc) include 2,3-, 2,4-, 2,5-, 2,6-, 3,4- and 3,5-substituted compounds.
**The structure $=P(O)-$ indicates that two bonds are occupied by $OR^{15}$.
***Structures 7 and 8 have a single $OR^{15}$ group linked as shown instead of two linked $OR^{15}$ groups.

Compounds listed in Table 2 are designated herein by numbers assigned to $(OR^{15})_2$ (where each $R^{15}$ is the same), Z and B according to the following convention, $R^{15}$.Z.B. The compound designations follows the scheme used in Table 1. Exemplary compounds include 1.1.1, 2.1.1, 3.1.1, 4.1.1, 5.1.1, 6.1.1, 7.1.1, 8.1.1, 9.1.1, 10.1.1, 11.1.1, 12.1.1, 13.1.1, 14.1.1, 15.1.1, 16.1.1, 1.2.1, 2.2.1, 3.2.1, 4.2.1, 5.2.1, 6.2.1, 7.2.1, 8.2.1, 9.2.1, 10.2.1, 11.2.1, 12.2.1, 13.2.1, 14.2.1, 15.2.1, 16.2.1, 1.3.1, 2.3.1, 3.3.1, 4.3.1, 5.3.1, 6.3.1, 7.3.1, 8.3.1, 9.3.1, 10.3.1, 11.3.1, 12.3.1, 13.3.1, 14.3.1, 15.3.1, 16.3.1, 1.4.1, 2.4.1, 3.4.1, 4.4.1, 5.4.1, 6.4.1, 7.4.1, 8.4.1, 9.4.1, 10.4.1, 11.4.1, 12.4.1, 13.4.1, 14.4.1, 15.4.1, 16.4.1, 1.5.1, 2.5.1, 3.5.1, 4.5.1, 5.5.1, 6.5.1, 7.5.1, 8.5.1, 9.5.1, 10.5.1, 11.5.1, 12.5.1, 13.5.1, 14.5.1, 15.5.1, 16.5.1, 1.6.1, 2.6.1, 3.6.1, 4.6.1, 5.6.1, 6.6.1, 7.6.1, 8.6.1, 9.6.1, 10.6.1, 11.6.1, 12.6.1, 13.6.1, 14.6.1, 15.6.1, 16.6.1, 1.7.1, 2.7.1, 3.7.1, 4.7.1, 5.7.1, 6.7.1, 7.7.1, 8.7.1, 9.7.1, 10.7.1, 11.7.1, 12.7.1, 13.7.1, 14.7.1, 15.7.1, 16.7.1, 1.8.1, 2.8.1, 3.8.1, 4.8.1, 5.8.1, 6.8.1, 7.8.1, 8.8.1, 9.8.1, 10.8.1, 11.8.1, 12.8.1, 13.8.1, 14.8.1, 15.8.1, 16.8.1, 1.1.2, 2.1.2, 3.1.2, 4.1.2, 5.1.2, 6.1.2, 7.1.2, 8.1.2, 9.1.2, 10.1.2, 11.1.2, 12.1.2, 13.1.2, 14.1.2, 15.1.2, 16.1.2, 1.2.2, 2.2.2, 3.2.2, 4.2.2, 5.2.2, 6.2.2, 7.2.2, 8.2.2, 9.2.2, 10.2.2, 11.2.2, 12.2.2, 13.2.2, 14.2.2, 15.2.2, 16.2.2, 1.3.2, 2.3.2, 3.3.2, 4.3.2, 5.3.2, 6.3.2, 7.3.2, 8.3.2, 9.3.2, 10.3.2, 11.3.2, 12.3.2, 13.3.2, 14.3.2, 15.3.2, 16.3.2, 1.4.2, 2.4.2, 3.4.2, 4.4.2, 5.4.2, 6.4.2, 7.4.2, 8.4.2, 9.4.2, 10.4.2, 11.4.2, 12.4.2, 13.4.2, 14.4.2, 15.4.2, 16.4.2, 1.5.2, 2.5.2, 3.5.2, 4.5.2, 5.5.2, 6.5.2, 7.5.2, 8.5.2, 9.5.2, 10.5.2, 11.5.2, 12.5.2, 13.5.2, 14.5.2, 15.5.2, 16.5.2, 1.6.2, 2.6.2, 3.6.2, 4.6.2, 5.6.2, 6.6.2, 7.6.2, 8.6.2, 9.6.2, 10.6.2, 11.6.2, 12.6.2, 13.6.2, 14.6.2, 15.6.2, 16.6.2, 1.7.2, 2.7.2, 3.7.2, 4.7.2, 5.7.2, 6.7.2, 7.7.2, 8.7.2, 9.7.2, 10.7.2, 11.7.2, 12.7.2, 13.7.2, 14.7.2, 15.7.2, 16.7.2, 1.8.2, 2.8.2, 3.8.2, 4.8.2, 5.8.2, 6.8.2, 7.8.2, 8.8.2, 9.8.2, 10.8.2, 11.8.2, 12.8.2, 13.8.2, 14.8.2, 15.8.2, 16.8.2, 1.1.3, 2.1.3, 3.1.3, 4.1.3, 5.1.3, 6.1.3, 7.1.3, 8.1.3, 9.1.3, 10.1.3, 11.1.3, 12.1.3, 13.1.3, 14.1.3, 15.1.3, 16.1.3, 1.2.3, 2.2.3, 3.2.3, 4.2.3, 5.2.3, 6.2.3, 7.2.3, 8.2.3, 9.2.3, 10.2.3, 11.2.3, 12.2.3, 13.2.3, 14.2.3, 15.2.3, 16.2.3, 1.3.3, 2.3.3, 3.3.3, 4.3.3, 5.3.3, 6.3.3, 7.3.3, 8.3.3, 9.3.3, 10.3.3, 11.3.3, 12.3.3, 13.3.3, 14.3.3, 15.3.3, 16.3.3, 1.4.3, 2.4.3, 3.4.3, 4.4.3, 5.4.3, 6.4.3, 7.4.3, 8.4.3, 9.4.3, 10.4.3, 11.4.3, 12.4.3, 13.4.3, 14.4.3, 15.4.3, 16.4.3, 1.5.3, 2.5.3, 3.5.3, 4.5.3, 5.5.3, 6.5.3, 7.5.3, 8.5.3, 9.5.3, 10.5.3, 11.5.3, 12.5.3, 13.5.3, 14.5.3, 15.5.3, 16.5.3, 1.6.3, 2.6.3, 3.6.3, 4.6.3, 5.6.3, 6.6.3, 7.6.3, 8.6.3, 9.6.3, 10.6.3, 11.6.3, 12.6.3, 13.6.3, 14.6.3, 15.6.3, 16.6.3, 1.7.3, 2.7.3, 3.7.3, 4.7.3, 5.7.3, 6.7.3, 7.7.3, 8.7.3, 9.7.3, 10.7.3, 11.7.3, 12.7.3, 13.7.3, 14.7.3, 15.7.3, 16.7.3, 1.8.3, 2.8.3, 3.8.3, 4.8.3, 5.8.3, 6.8.3, 7.8.3, 8.8.3, 9.8.3, 10.8.3, 11.8.3, 12.8.3, 13.8.3, 14.8.3, 15.8.3, 16.8.3, 1.1.4, 2.1.4, 3.1.4, 4.1.4, 5.1.4, 6.1.4, 7.1.4, 8.1.4, 9.1.4, 10.1.4, 11.1.4, 12.1.4, 13.1.4, 14.1.4, 15.1.4, 16.1.4, 1.2.4, 2.2.4, 3.2.4, 4.2.4, 5.2.4, 6.2.4, 7.2.4, 8.2.4, 9.2.4, 10.2.4, 11.2.4, 12.2.4, 13.2.4, 14.2.4, 15.2.4, 16.2.4, 1.3.4, 2.3.4, 3.3.4, 4.3.4, 5.3.4, 6.3.4, 7.3.4, 8.3.4, 9.3.4, 10.3.4, 11.3.4, 12.3.4, 13.3.4, 14.3.4, 15.3.4, 16.3.4, 1.4.4, 2.4.4, 3.4.4, 4.4.4, 5.4.4, 6.4.4, 7.4.4, 8.4.4, 9.4.4, 10.4.4, 11.4.4, 12.4.4, 13.4.4, 14.4.4, 15.4.4, 16.4.4, 1.5.4, 2.5.4, 3.5.4, 4.5.4, 5.5.4, 6.5.4, 7.5.4, 8.5.4, 9.5.4, 10.5.4, 11.5.4, 12.5.4, 13.5.4, 14.5.4, 15.5.4, 16.5.4, 1.6.4, 2.6.4, 3.6.4, 4.6.4, 5.6.4, 6.6.4, 7.6.4, 8.6.4, 9.6.4, 10.6.4, 11.6.4, 12.6.4, 13.6.4, 14.6.4, 15.6.4, 16.6.4, 1.7.4, 2.7.4, 3.7.4, 4.7.4, 5.7.4, 6.7.4, 7.7.4, 8.7.4, 9.7.4, 10.7.4, 11.7.4, 12.7.4, 13.7.4, 14.7.4, 15.7.4, 16.7.4, 1.8.4, 2.8.4, 3.8.4, 4.8.4, 5.8.4, 6.8.4, 7.8.4, 8.8.4, 9.8.4, 10.8.4, 11.8.4, 12.8.4, 13.8.4, 14.8.4, 15.8.4, 16.8.4, 1.1.5, 2.1.5, 3.1.5, 4.1.5, 5.1.5, 6.1.5, 7.1.5, 8.1.5, 9.1.5, 10.1.5, 11.1.5, 12.1.5, 13.1.5, 14.1.5, 15.1.5, 16.1.5, 1.2.5, 2.2.5, 3.2.5, 4.2.5, 5.2.5, 6.2.5, 7.2.5, 8.2.5, 9.2.5, 10.2.5, 11.2.5, 12.2.5, 13.2.5, 14.2.5, 15.2.5, 16.2.5, 1.3.5, 2.3.5, 3.3.5, 4.3.5, 5.3.5, 6.3.5, 7.3.5, 8.3.5, 9.3.5, 10.3.5, 11.3.5, 12.3.5, 13.3.5, 14.3.5, 15.3.5, 16.3.5, 1.4.5, 2.4.5, 3.4.5, 4.4.5, 5.4.5, 6.4.5, 7.4.5, 8.4.5, 9.4.5, 10.4.5, 11.4.5, 12.4.5, 13.4.5, 14.4.5, 15.4.5, 16.4.5, 1.5.5, 2.5.5, 3.5.5, 4.5.5, 5.5.5, 6.5.5, 7.5.5, 8.5.5, 9.5.5, 10.5.5, 11.5.5, 12.5.5, 13.5.5, 14.5.5, 15.5.5, 16.5.5, 1.6.5, 2.6.5, 3.6.5, 4.6.5, 5.6.5, 6.6.5, 7.6.5, 8.6.5, 9.6.5, 10.6.5, 11.6.5, 12.6.5, 13.6.5, 14.6.5, 15.6.5, 16.6.5, 1.7.5, 2.7.5, 3.7.5, 4.7.5, 5.7.5, 6.7.5, 7.7.5, 8.7.5, 9.7.5, 10.7.5, 11.7.5, 12.7.5, 13.7.5, 14.7.5, 15.7.5, 16.7.5, 1.8.5, 2.8.5, 3.8.5, 4.8.5, 5.8.5, 6.8.5, 7.8.5, 8.8.5, 9.8.5, 10.8.5, 11.8.5, 12.8.5, 13.8.5, 14.8.5, 15.8.5, 16.8.5, 1.1.6, 2.1.6, 3.1.6, 4.1.6, 5.1.6, 6.1.6, 7.1.6, 8.1.6, 9.1.6, 10.1.6, 11.1.6, 12.1.6, 13.1.6, 14.1.6, 15.1.6, 16.1.6, 1.2.6, 2.2.6, 3.2.6, 4.2.6, 5.2.6, 6.2.6, 7.2.6, 8.2.6, 9.2.6, 10.2.6, 11.2.6, 12.2.6, 13.2.6, 14.2.6, 15.2.6, 16.2.6, 1.3.6, 2.3.6, 3.3.6, 4.3.6, 5.3.6, 6.3.6, 7.3.6, 8.3.6, 9.3.6, 10.3.6, 11.3.6, 12.3.6, 13.3.6, 14.3.6, 15.3.6, 16.3.6, 1.4.6, 2.4.6, 3.4.6, 4.4.6, 5.4.6, 6.4.6, 7.4.6, 8.4.6, 9.4.6, 10.4.6, 11.4.6, 12.4.6, 13.4.6, 14.4.6, 15.4.6, 16.4.6, 1.5.6, 2.5.6, 3.5.6, 4.5.6, 5.5.6, 6.5.6, 7.5.6, 8.5.6, 9.5.6, 10.5.6, 11.5.6, 12.5.6, 13.5.6, 14.5.6, 15.5.6, 16.5.6, 1.6.6, 2.6.6, 3.6.6, 4.6.6, 5.6.6, 6.6.6, 7.6.6, 8.6.6, 9.6.6, 10.6.6, 11.6.6, 12.6.6, 13.6.6, 14.6.6, 15.6.6, 16.6.6, 1.7.6, 2.7.6, 3.7.6, 4.7.6, 5.7.6, 6.7.6, 7.7.6, 8.7.6, 9.7.6, 10.7.6, 11.7.6, 12.7.6, 13.7.6, 14.7.6, 15.7.6, 16.7.6, 1.8.6, 2.8.6, 3.8.6, 4.8.6, 5.8.6, 6.8.6, 7.8.6, 8.8.6, 9.8.6, 10.8.6, 11.8.6, 12.8.6, 13.8.6, 14.8.6, 15.8.6, 16.8.6, 1.1.7, 2.1.7, 3.1.7, 4.1.7, 5.1.7, 6.1.7, 7.1.7, 8.1.7, 9.1.7, 10.1.7, 11.1.7, 12.1.7, 13.1.7, 14.1.7, 15.1.7, 16.1.7, 1.2.7, 2.2.7, 3.2.7, 4.2.7, 5.2.7, 6.2.7, 7.2.7, 8.2.7, 9.2.7, 10.2.7, 11.2.7, 12.2.7, 13.2.7, 14.2.7, 15.2.7, 16.2.7, 1.3.7, 2.3.7, 3.3.7, 4.3.7, 5.3.7, 6.3.7, 7.3.7, 8.3.7, 9.3.7, 10.3.7, 11.3.7, 12.3.7, 13.3.7, 14.3.7, 15.3.7, 16.3.7, 1.4.7, 2.4.7, 3.4.7, 4.4.7, 5.4.7, 6.4.7, 7.4.7, 8.4.7, 9.4.7, 10.4.7, 11.4.7, 12.4.7, 13.4.7, 14.4.7, 15.4.7, 16.4.7, 1.5.7, 2.5.7, 3.5.7, 4.5.7, 5.5.7, 6.5.7, 7.5.7, 8.5.7, 9.5.7, 10.5.7, 11.5.7, 12.5.7, 13.5.7, 14.5.7, 15.5.7, 16.5.7, 1.6.7, 2.6.7, 3.6.7, 4.6.7, 5.6.7, 6.6.7, 7.6.7, 8.6.7, 9.6.7, 10.6.7, 11.6.7, 12.6.7, 13.6.7, 14.6.7, 15.6.7, 16.6.7, 1.7.7, 2.7.7, 3.7.7, 4.7.7, 5.7.7, 6.7.7, 7.7.7, 8.7.7, 9.7.7, 10.7.7, 11.7.7, 12.7.7, 13.7.7, 14.7.7, 15.7.7, 16.7.7, 1.8.7, 2.8.7, 3.8.7, 4.8.7, 5.8.7, 6.8.7, 7.8.7, 8.8.7, 9.8.7, 10.8.7, 11.8.7, 12.8.7, 13.8.7, 14.8.7, 15.8.7 and 16.8.7.

One determines the suitability of the presence or absence of any particular $R^{15}$ group by stability and/or bioavailability assays (e.g., stability assay in aqueous conditions such as low pH/intestinal lumen conditions or assay in the presence of cellular extracts containing esterases or by bioavailability assay using animal models) known in the art. The skilled artisan routinely performs these assays.

The NPEs generally can comprise a protected heterocyclic base. These compounds are useful as synthetic intermediates and/or, as therapeutic agents per se. Protected heterocyclic base compounds structures, their isomers, tautomers and the salts of such compounds having the formula (5)

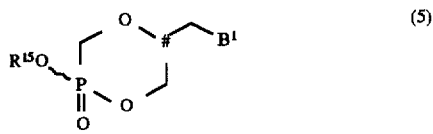

(5)

where $B^1$ is a protected heterocyclic base.

The exemplary reaction schemes used to synthesize protected heterocyclic base compounds shown below utilize cHPMPC as an example. Analogous reactions will generate compounds comprising other bases such as adenine. Phosphonate alkyl and aryl esters of compounds comprising $B^1$ are prepared, using HPMPC and cHPMPC as an example, according to the following procedures

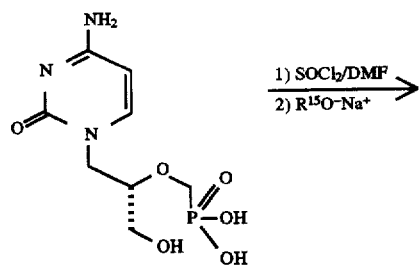

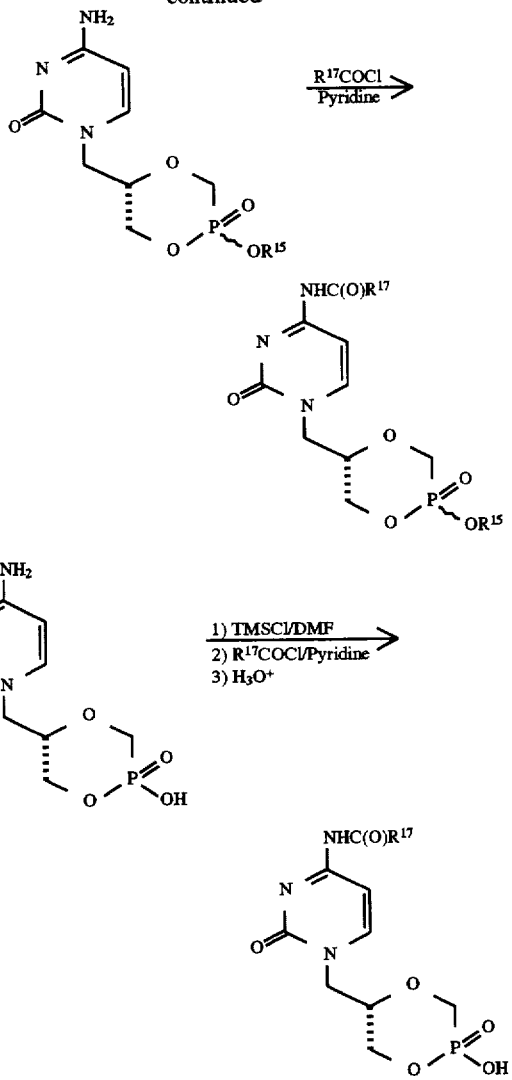

wherein $R^{17}$ is $C_{1-10}$ alkyl. Either procedure is readily adapted to synthesizing compounds containing protected heterocyclic bases other than cytosine, e.g., adenine, guanine, 2,6-diaminopurine or 2-aminopurine. Exemplary $R^{15}$ and/or $R^{17}$, which can be the same or different, include phenyl, substituted phenyl, —$C_{10}H_{15}$ (where $C_{10}H_5$ is adamantoyl), —$CH_2$—$C_6H_5$, —$C_6H_5$, —$(CH_3)_3$, —CH$(CH_3)_2$, —$CH_2CH_3$, methyl, ethyl, butyl, t-butyl, heptanyl, nonanyl, undecanyl, lauryl, steryl, undecenyl and the like. The amide linkage is conveniently formed by reaction of the acyl chloride with the exocyclic amine linked to the base. When $R^{15}$ is linked to the free phosphonate the resulting ester will comprise a single isomer or a racemic mixture at the phosphorus atom. Low temperature reaction conditions (lower than about −20°, e.g., about −20° to about −40° C. or about −40° to about −80°C.) tend to favor single isomer products, while reaction at higher temperatures (above about −20°, e.g. −20° to 40° C.) generally results in a racemic mix. When a racemic mixture is obtained, the isomers can be conveniently separated by, for example, HPLC, although the mixture can be used, for example, as a synthetic intermediate or as an active antimicrobial agent, without resolution. Synthesis of the phenyl ester of cHPMPC at −78° C. by reaction of the chloridate and phenoxide yielded a racemic mixture consisting of about >90% of the product as one isomer (isomer #1) at the phosphorus atom while the remaining ~≦10% was present as the other isomer (isomer #2). The racemic mixture was converted to isomer #2 (≧90%) by incubation at room temperature for about 10 minutes (about 10 to 30 minutes is generally suitable) with a catalytic amount of sodium phenoxide in DMF. This method can be used to convert one isomer of cHPMP-B or cHPMP-B$^1$ (such as cHPMPC or cHPMPA) aryloxy or alkoxy ester to the other isomer with catalytic amounts of the corresponding aryloxide ion or alkoxide ion.

The cHPMPC pivaloyloxymethyl ester synthesis yields a racemic mixture at the phosphorus atom. The mixture was separated by HPLC into the two isomers which were then exposed to an rat intestinal homogenate or to a rat intestinal wash. One of the isomers was converted to cHPMPC after incubation in the homogenate while the other isomer was converted to HPMPC pivaloyloxymethyl monoester. Both isomers were converted to HPMPC pivaloyloxymethyl monoester after incubation in the intestinal wash. These results suggested that (1) in at least some cases, enzyme activity can have a differential effect on the metabolic fate of a cHPMPC ester depending on which phosphorus isomer is present and (2) chemical activity (i.e., the acidity of the intestinal wash) can affect the metabolic fate of a given compound in a manner that differs from enzyme activity.

A method to obtain heterocyclic bases comprising the C(O)R$^{17}$ protecting group is accomplished as follows using the acyl chloride (R$^{17}$C(O)Cl) using HPMPC and cHPMPC as an example wherein Tr is the hydroxyl protecting group trityl. The detritylation step is accomplished by acid treatment, such as 80% acetic acid at about 10° to 60° C. for 1–2 hours. The R$^{15}$ moiety is removed using a Lewis acid such as TMSBr to yield the free phosphonate.

Phosphonate compounds comprising B$^1$ and a C$_{2-20}$ 1-acyloxy-1-alkyl or a C$_{4-20}$ 1-acyloxy-1-alkyl-1-aryl ester group are prepared as follows

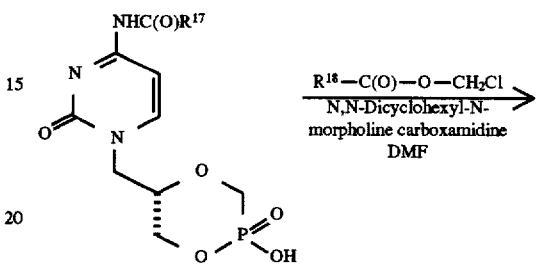

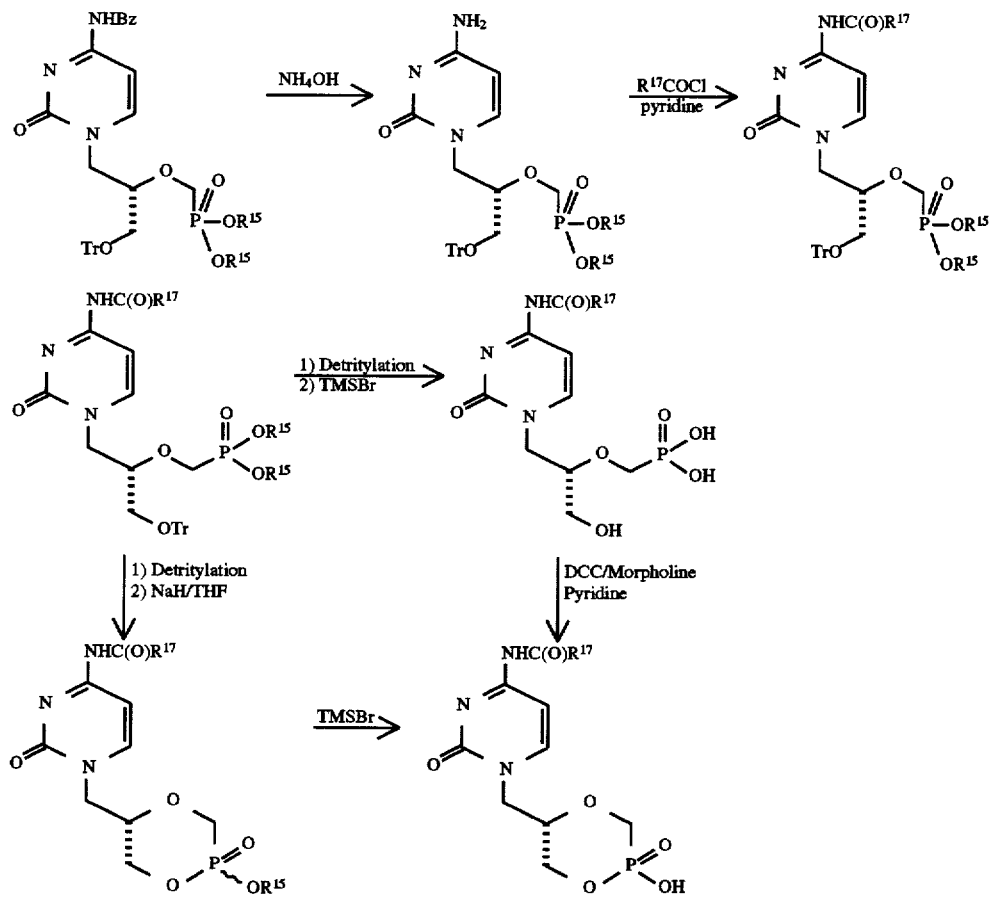

-continued

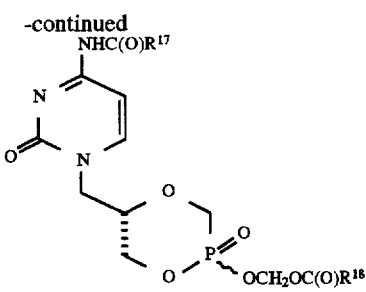

wherein $R^{18}$ is $C_{1-20}$ alkyl which is unsubstituted or substituted by substituents independently selected from the group consisting of $C_{1-6}$ alkyl, $C_{1-6}$ alkoxy, $C_{1-6}$ haloalkyl (1 to 3 halogen atoms), cyano, nitro, OH, O, NH and halogen (including ethyl, propyl, isopropyl, t-butyl, isobutyl and adamantoyl), or $C_{3-10}$ aryl which is unsubstituted or substituted by substituents independently selected from the group consisting of $C_{1-6}$ alkyl, $C_{1-6}$ alkoxy, $C_{1-6}$ haloalkyl (1 to 3 halogen atoms), cyano, nitro, OH, O, N and halogen (including phenyl, and 3- or 4-pyridyl).

The amine protecting group $=CR^{19}N(R^{20})_2$, where $R^{19}$ is hydrogen or $CH_3$ and $R^{20}$ is $C_{1-10}$ alkyl, or both $R^{20}$ together are 1-morpholino, 1-piperidine or 1-pyrrolidine, is incorporated into an exocyclic amine to yield protected heterocyclic base compounds as follows

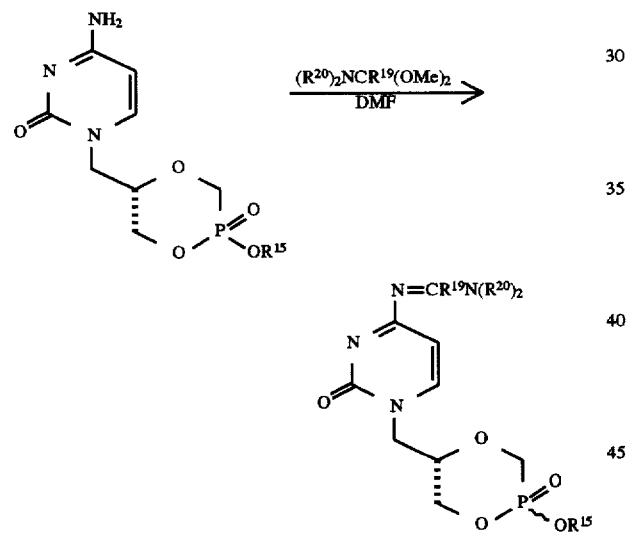

Exemplary $R^{20}$ alkyl groups include methyl, ethyl, propyl, isopropyl, cyclopropyl, butyl, isobutyl, t-butyl and cyclobutyl. In general, both $R^{20}$ alkyl groups will be the same. The reaction can be carried out in dry DMF at room temperature (about 20°–30° C.) as previously described (Kerr et al *J. Pharm. Sci.* (1994) 83:582; Kerr et al *J. Med. Chem.* (1992) 35:1996), or DMF can be substituted with $CH_3CN$ and 4 Å molecular sieves. Protected heterocyclic bases where $R^{19}$ is hydrogen are stable under neutral anhydrous conditions and are generally labile under acidic aqueous conditions. When $R^{19}$ is methyl, the protecting group is more stable to aqueous acidic or basic conditions.

Table 3 lists $R^{15}$ ester and other moieties that can be incorporated into the phosphorus atom of both cyclic moieties (such as cHPMPC comprising a protected heterocyclic base or cHPMPC) or linear moieties (such as HPMPC comprising a protected heterocyclic base or PMEA comprising a protected heterocyclic base or PMEA). Esters of Table 3 structures 1–5, 8–10 and 16, 17, 19–22 are synthesized by reacting a nucleotide analog (such as cHPMPC) the corresponding halide (chloride or acyl chloride and the like) and N ,N-dicylohexyl-N-morpholine carboxamidine (or another base such as DBU, triethylamine, $CsCO_3$, N,N-dimethylaniline and the like) in DMF (or other solvent such as acetonitrile or N-methylpyrrolidone). Esters of structures 5–7, 11, 12, 21, and 23–26 are synthesized by reaction of the alcohol or alkoxide salt (or the corresponding amines in the case of compounds such as 13, 14 and 15) with a nucleotide analog monochlorophosphonate or dichlorophosphonate (such as cHPMPC monochlorophosphonate or PMEA dichlorophosphonate) or another activated phosphonate.

TABLE 3

| | |
|---|---|
| 1. | $-CH_2-C(O)-N(R^C)_2$* |
| 2. | $-CH_2-S(O)(R^C)$ |
| 3. | $-CH_2-S(O)_2(R^C)$ |
| 4. | $-CH_2-C(O)-CH_2-C_6H_5$ |
| 5. | 3-cholesteryl |
| 6. | 3-pyridyl |
| 7. | N-ethylmorpholino |
| 8. | $-CH_2-O-C(O)-C_6H_5$ |
| 9. | $-CH_2-O-C(O)-CH_2CH_3$ |
| 10. | $-CH_2-O-C(O)-C(CH_3)_3$ |
| 11. | $-CH_2-CCl_3$ |
| 12. | $-C_6H_5$ |
| 13. | $-NH-CH_2-C(O)O-CH_2CH_3$ |
| 14. | $-N(CH_3)-CH_2-C(O)O-CH_2CH_3$ |
| 15. | $-NHR^D$* |
| 16. | $-CH_2-O-C(O)-C_{10}H_{15}$ |
| 17. | $-CH_2-O-C(O)-CH(CH_3)_2$ |
| 18. | $-CH_2-C\#H(OC(O)CH_2R^C)-CH_2-(OC(O)CH_2R^C)$** |
| 19. | —CH₂C(O)N⟨morpholine⟩ |
| 20. | [structure] |
| 21. | [structure] |
| 22. | —CH₂—O—C(O)—[pyridyl] |
| 23. | —CH₂CH₂—[pyridyl] |
| 24. | CH₃O(O)C—[structure] |

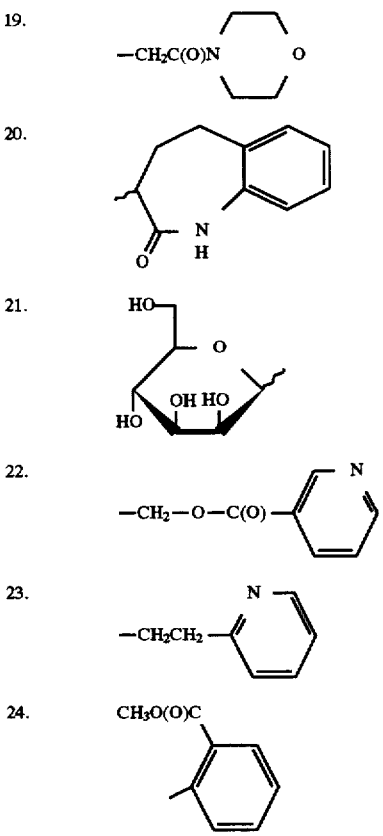

TABLE 3-continued

25. CH₃CH₂O(O)C— [structure: toluene ring with ethyl ester and methyl substituents]

26. —CH₂— [structure: benzene ring with three OCH₃ groups at 2,4,5 positions]

*RD is $C_{1-20}$ alkyl, including $C_{4-16}$ alkyl.
**Each $R^C$ is the same or different (includes methyl, ethyl, propyl, isopropyl and t-butyl).

All citations are hereby expressly incorporated by reference. The following examples are illustrative and do not limit the scope of this invention.

EXAMPLE 1

Synthesis of phosphonate amidate compounds

The compounds of structural formula Id shown are in Table 6 (bis(glycyl benzyl ester)PMEA (compound Ex 4), bis(alanyl benzyl ester)PMEA (Ex 1), bis(phenylalanyl benzyl ester)PMEA (Ex 5), etc. Compounds Ex 1–Ex 12 were synthesized by the following procedure. PMEA (Z—B═—CH₂—O—CH₂—CH₂—B, where B is adenin-9-yl) (0.3 g; 1.1 mmol) and amino acid ester.HCl (2.2 mmol; Sigma) were suspended in dry pyridine (6 mL) containing triethylamine (0.3 mL; 22.2 mmol), followed by addition to a mixture of freshly prepared triphenylphosphine (3.3 mmol) and 2,2'-dipyridyl disulfide (3.3 mmol) in pyridine (3 mL). The mixture was stirred at room temperature overnight, concentrated and partitioned between methylene chloride and water. The organic solution was dried over MgSO₄, concentrated and purified by flash column chromatography on silica gel.

Ex 14 was synthesized using freshly prepared triphenylphosphine (6.0 mmol) and 2,2'-dipyridyl disulfide (6.0 mmol) in pyridine (20 mL) at room temperature to which PMEA (2.0 mmol) was added. The suspension was stirred for 10 min. and ethyl sarcosine HCl (N-methylglycine HCl ethyl ester; 1.2 g, 8.0 mmol) was added. The suspension was warmed to 90° C. and stirred for 24 hours. Crude product was concentrated by rotary evaporation and purified by silica flash chromatography (mobile phase 1% methanol gradient to 20% methanol/80% methylene chloride).

Compound Ex 13 was synthesized in a similar manner using PMEA and phenylalanine N-ethylmorpholino ester.

TABLE 6

| Compound | L¹ |
| --- | --- |
| Ex 1 | -NH-CH(CH₃)-C(O)OCH₂C₆H₅ |
| Ex 2 | -NH-CH(CH₂C₆H₅)-C(O)OCH₂C₆H₅ |
| Ex 3 | -NH-CH(CH₂CH(CH₃)₂)-C(O)OCH₂C₆H₅ |
| Ex 4 | -NH-CH₂-C(O)OCH₂C₆H₅ |
| Ex 5 | -NH-CH(CH₃)-C(O)OC₂H₅ |
| Ex 6 | -NH-CH(CH₂CH(CH₃)₂)-C(O)OC₂H₅ |
| Ex 7 | -NH-CH₂-C(O)OC₂H₅ |
| Ex 8 | -NH-CH(CH₂C₆H₅)-C(O)OC(CH₃)₃ |
| Ex 9 | -NH-CH(CH₂CH(CH₃)₂)-C(O)OC(CH₃)₃ |
| Ex 10 | -NH-CH(CH₃)-C(O)OC(CH₃)₃ |

TABLE 6-continued

| Compound | L¹ |
| --- | --- |
| Ex 11 | -NH-CH₂-C(O)OC(CH₃)₃ |
| Ex 12 | -NH-CH(CH₂C₆H₅)-C(O)OC₂H₅ |
| Ex 13 | -NH-CH(CH₂C₆H₅)C(O)O-(CH₂)₂-N[(CH₂)₂(CH₂)₂]O |
| Ex 14 | -N(CH₃)-CH₂-C(O)OC₂H₅ |

EXAMPLE 2

Antiviral activity

Compounds were individually tested for activity against HSV-1 and/or HSV-2. HSV-2 (strain 414-92) was tested using MA 104 cells in the following assay protocol. 96-Well plates were seeded with 1×10⁴ MA 104 cells per well using 200 μL minimal essential medium (MEM) containing 10% calf serum per well, and incubated overnight at 37° C. The compounds were dissolved in MEM Earle's Salts without serum. The medium was removed by aspiration and 100 μL MEM Earle's Salts without serum was added to the wells. Serial 3-fold dilutions of the compounds were prepared by serial transfer of 50 μL of medium from wells containing compound to wells lacking compound. The plates were incubated 15 minutes at 37° C. followed by addition of 100 PFU/well of virus in MEM Earle's Salts with 2% fetal bovine serum. The plates were then incubated at 37° C. for three days until approximately 90% of the cells in virus infected control wells containing no compound were killed. Following incubation, medium was aspirated and the wells were washed with sterile PBS. 100 μL 0.5% crystal violet in 20% methanol was then added to the wells for 5 minutes, aspirated and the wells were washed two or three times with distilled water. 200 μL of 0.01 N HCl was added to the wells and the absorbance of each well at 595 nm was determined. The results, shown in Table 6, were expressed as the IC₅₀, the concentration (μM) that inhibits cell killing mediated by HSV-2 by 50%. IC₅₀ values varied from 2 μM to >100 μM compared to an IC₅₀ for PMEA of 21 μM. Thus, some of the compounds were more active against HSV-1 than PMEA. The toxicity of the compounds were expressed as the CC₅₀, the concentration that kills 50% of uninfected cells.

The compounds were also tested for activity against the KOS strain of HSV-1 in VERO cells. The results, shown in Table 7, were expressed as the EC₅₀, the concentration (μM) that inhibits cell killing mediated by HSV-2 by 50%. EC₅₀ values varied from 2 μM to >200 μM compared to an EC₅₀ for PMEA of 138 μM. Thus, some of the compounds were more active against HSV-2 than PMEA.

TABLE 7

| | HSV-1 | HSV-2 | |
| --- | --- | --- | --- |
| compound | EC₅₀ | IC₅₀ | CC₅₀ |
| Ex 7 | >200 | >100 | >100 |
| Ex 5 | nt* | >100 | >100 |
| Ex 6 | 20 | 33 | >100 |
| Ex 12 | nt | 20 | 80 |
| Ex 11 | >200 | >100 | >100 |
| Ex 10 | >200 | >100 | >100 |
| Ex 9 | 63 | 63 | >100 |
| Ex 8 | 3 | 9 | 20 |
| Ex 4 | nt | 60 | >100 |
| Ex 1 | nt | 20 | >100 |

TABLE 7-continued

| compound | HSV-1 EC$_{50}$ | HSV-2 IC$_{50}$ | HSV-2 CC$_{50}$ |
|---|---|---|---|
| Ex 3 | nt | 2 | 30 |
| Ex 2 | nt | 4 | 20 |

EXAMPLE 3

PMEA, monophenyl ester, mono N-ethylmorpholinophenylalanyl phosphoroamidate

Bis(phenyl)PMEA is selectively hydrolyzed to the monophenyl ester of PMEA using NaOH in THF. The reaction mixture is neutralized with acid (1 N HCl), and the monophenyl PMEA is isolated by filtration. The anhydrous monophenyl PMEA and 2 equivalents of a freshly prepared 1:1 mixture of triphenylphosphine and 2,2'-dipyridyl disulfide in pyridine is condensed with 1 equivalent of phenylalanine N-ethyl-morpholino ester in triethylamine and pyridine to afford the title compound. The title compound is recovered by evaporation of the solvents under reduced pressure and purified by silica gel chromatography.

EXAMPLE 4

Antiviral activity of PMEA esters

PMEA and PMEA esters were tested for inhibition of cytopathic effects by HSV II in MA 104 cells as described except that CPE was determined after incubation with virus by addition of 100 µL XTT, 1 mg/mL in deficient DME containing 25 µM PMF followed by measuring absorbance. The esters tested were bis(POM)PMEA, bis(phenyl)PMEA, monophenylPMEA, bis(3-dimethylaminophenyl)PMEA, bis(3-methoxyphenyl)PMEA, bis(2-carboethoxyphenyl) PMEA, bis(adamantoyl oxymethyl)PMEA, bis(4-fluorophenyl)PMEA and bis(2-ethoxyphenyl)PMEA. All of the compounds tested were active, which indicated that the ester groups were removed, thereby allowing free PMEA to inhibit virus replication and/or cytopathic effects. The IC$_{50}$ and CC$_{50}$ of PMEA in the assay was 19.3 µM and 2000 µM respectively and the IC$_{50}$ and CC$_{50}$ of bis(POM)PMEA in the assay was 0.5 µM and >10 µM respectively. IC$_{50}$ values for the mono and bis esters ranged from 1.1 µM to 67.5 µM and the CC$_{50}$ values ranged from 70 µM to 500 µM.

EXAMPLE 5

Oral bioavailability of nucleotide analog amidates and PMEA esters

Nucleotide analog amidates and nucleotide analogs are tested for their bioavailabililty when administered to cynomologous (or rhesus) monkeys by oral, subcutaneous or intramuscular routes. Bioavailability is determined by measuring PMEA levels in plasma or urine at different times after administering the drug using radiolabeled ($^3$H, $^{14}$C, etc) compound or, for compounds having adenine, essentially as described (Naesens, et al., *Clin Chem* (1992) 38:480–485; Russell, et al., *J Chromatogr (Netherlands)* (1991) 572:321–326). Radiolabeled compounds are obtained commercially (Moravek Biochemicals, Brea, Calif.) or by standard procedures, such as catalytic hydrogen exchange for $^3$H labeling. Compounds such as bis(2-ethoxyphenyl)PMEA, bis(2-carboethoxyphenyl)PMEA, bis(O-benzylphenylalanyl)PMEA, bis(3,5-dimethoxyphenyl)PMEA, bis(4-fluorophenyl)PMEA, bis(adamantoyl oxymethyl)PMEA, bis(phenyl)PMEA, bis(3-methoxyphenyl)PMEA are tested for oral bioavailability by administering about 10–30 mg/Kg (usually 15 to 25 mg/Kg) containing about 20–50 µCi/Kg (usually about 40 µCi/Kg) of radiolabeled compound, followed by withdrawing blood samples at several times after administration (exemplary time points are 0.1, 0.25, 0.5, 1.0, 1.5, 2.0, 2.5, 3.0, 4, 6, 12, 18, 24, 36, 48, 72, 96 hours after administration), obtaining plasma and determining the amount of radiolabeled compound present per volume (about 0.1–1.0 mL) of serum. Oral bioavailability of the tested compounds is 2–80% (or any value between 2% and 80% in 1% increments), preferably 10–80% and more preferably 15 to 80%. The oral bioavailability of bis(POM)PMEA by this type of assay is typically about 25% in monkeys and PMEA is about 2–4% (Balzarini et al., *Animal Models in AIDS* (1990) p. 131–138, Schellekens, H. et al (ed), Elsevier Science Publications, Amsterdam) while nucleotide analog amidates and nucleotide analogs (including mono- and diesters) can have oral bioavailabilities of about 5%, 10%, 15%, 30%, 40%, 50%, 60% or 80%.

Total radioactivity in plasma is determined by mixing about 200 µL of plasma with a scintillation counting cocktail (such as 10 mL of Scinti-Safe plus LSC cocktail) and counting in a scintillation counter (usually for about 5–30 minutes). Detailed analysis of the radiochemical composition is accomplished using about 350 µL of plasma, denaturing proteins in the serum (using about 700 µL 0.1% trifluoroacetic acid in acetonitrile for example), drying the resulting sample under reduced pressure, suspending the sample in an appropriate buffer (for example using about 100 µL of 2% acetonitrile in 25 mM potassium phosphate buffer with 10 mM tetrabutyl ammonium hydrogen phosphate (TBAHP), pH 6.0 for HPLC analysis), centrifuging the sample and analyzing the supernatant for individual radiolabeled species by reverse phase HPLC on commercially available columns (The Separation Group, Hesperia, Calif.; Vydac C18, 5 µm, 250×4.6 mm column with an injection volume of about 50 µL and a flow rate of about 1.0 mL/min. at about 35° C. using buffer for 2 minutes followed by a linear gradient to about 65% acetonitrile in 25 mM potassium phosphate buffer with 10 mM TBAHP, pH 6.0 over 13 about minutes). Radiolabel detection is accomplished using means such as commercially available radioactive flow detection systems or scintillation counting systems (Packard, Meridian, Conn.).

Fluorescence detection of PMEA in plasma is accomplished by measuring fluorescence emission (420 nm, with excitation at about 236 nm) with a detector (model F2000, Spectra Physics, San Jose, Calif.) from the HPLC gradient essentially as described above (2 to 65% acetonitrile). Samples for analysis are prepared from plasma (200 µL) by protein precipitation with TFA (400 µL 0.1% in acetonitrile), drying and conversion of adenine to N6-ethenoadenine in 200 µL of reaction buffer (0.34% chloroacetaldehyde, 100 mM sodium acetate, pH 4.5) for 40 minutes at 95° C. followed by HPLC analysis using 50 µL.

EXAMPLE 6

Bis(adamantoyl oxymethyl)PMEA ester

DBU (1,8-diazabicyclo[5.4.0]undec-7-ene; 1.53 g, 10 mmol) was added to a suspension of PMEA (1.365 g, 5 mmol) in DMF (25 mL). Adamantoyl oxymethyl chloride (5.72 g, 25 mmol) in DMF (25 mL) was added to the reaction mixture which was then stirred for four days at room temperature and the volatiles were removed under vacuum. The crude product obtained after removal of the solvent was loaded onto a silica gel column and washed with 3% MeOH/CH$_2$Cl$_2$ to remove nonpolar impurities. 1 g (30%) of bis(adamantoyl oxymethyl)PMEA ester was eluted in 8% MeOH/CH$_2$Cl$_2$. Adamantoyl oxymethyl chloride was obtained by conversion of 1-adamantanecarbonyl chloride (Aldrich No. 11,772-2) with (CH$_2$O)$_n$/ZnCl$_2$ and has been described (Bodor, et al *J Med Chem* (1980) 23:474–480).

EXAMPLE 7

Bis(phenyl)PMEA and bis(2-ethoxyphenyl)PMEA esters

PMEA (2.0 g, 7.3 mmol), acetonitrile (20 mL), thionyl chloride (20 mL) and N,N-dimethylformamide (2 drops) were added to a 250 mL single neck round bottom flask equipped with a magnetic stirrer, water cooled condenser and N$_2$ atmosphere. The flask was immersed in a 85° C. oil bath and the resulting suspension was stirred for two hours. The resulting solution was then concentrated to dryness and acetonitrile (50 mL) was added to redissolve the crude chloridate.

To a separate 250 mL single neck round bottom flask equipped with a mechanical stirrer, and N$_2$ atmosphere, phenol (3.25 g, 35 mmol), tetrahydrofuran (80 mL) and sodium hydride (1.4 g, 34 mmol, 60% (w/w) dispersion in mineral oil) was charged. After stirring for 30 minutes, the solution was cooled to -78° C. with a dry ice-acetone bath. The acetonitrile from the previous step was then added drop-wise at a rate that the internal temperature did not rise above -76° C. After the addition was complete, the resulting suspension was poured into saturated aqueous NaHCO$_3$ (100 mL) and extracted with methylene chloride (3×150 mL). The combined organic extracts were washed with H$_2$O (100 mL), brine (100 mL) and dried with anhydrous Na$_2$SO$_4$. Concentration by rotary evaporation afforded a yellow solid. Purification by recrystallization (ethyl acetate/hexanes) afforded pure bis(phenyl)PMEA (1.64 g, 53%). Bis(2-ethoxyphenyl)PMEA was made similarly using 2-ethoxyphenol in place of phenol in 36% yield.

EXAMPLE 8

(R)-9-(2-Di2 ethoxyphenylphosphonylmethoxpropyl) adenine

To a solution of 2-ethoxyphenol (45 mmol, 6.22 g) in pyridine (75 mL) was added (R)-9-(2-phosphonylmethoxypropyl adenine (PMPA, 15 mmol, 4.3 g), creating a white suspension. A separate solution of 2,2'-dipyridyl disulfide (45 mmol, 9.91 g) and triphenyl phosphine (45 mmol, 11.81 g) in pyridine (75 mL) was added at 22° C. in a single portion to the white suspension. Then, triethylamine (30 mmol, 4.18 mL) was added in a single portion to the entire mixture, which was stirred at 75° C. for 21 h (TLC:10% MeOH/EtoAc). The dark amber slurry was then coevaporated with toluene (100 mL). It was then dissolved in dichloromethane (200 mL) and extracted twice with water (200 mL). The organic phase was dried (NaSO$_4$), filtered and concentrated (in vacuo) to a brown syrup (25.4 g). The syrup was purified by flash chromatography: 1–5% MeOH/EtoAc to elute impurities, then 6–12% MeOH/EtoAc (title compound elutes at 10–11%). The desired fractions were concentrated to afford 1.04 g of a brown solid. The solid was then recrystalized (EtoAc) to give the title compound (780 mg, 12% yield) as a tan solid. HNMR (CDCl$_3$) δ1.25 (d, J=7.5 Hz, 3H, CH$_3$), δ1.46 (m, 6H (OCH$_2$CH$_3$)$_2$), 4H (OCH$_2$CH$_3$)$_2$), δ3.9 (m, 2H, O—CH$_2$P), δ4.04 (m, 1H, H-2'), δ4.09–4.39 (m, 2H, H-1'), 7.24 (m8H, (C$_6$H$_4$)$_2$), 7.92 (S, 1H, (C$_8$—H), 8.19 (S, 1H, C$_2$—H).

EXAMPLE 9 cHPMPU cHPMPU was synthesized by adding thionyl chloride (60 mL, 0.812 mmol, 2.02 eq) dropwise to a suspension of disodium HPMPU (131 mg, 0.404 mmol) in N,N-dimethylformamide (1.25 mL) at ambient temperature. The resulting light-yellow solution was stirred for 20 min at ambient temperature and then concentrated to dryness (in vacuo, 45° C.). H20 (2 mL) was added and the resulting solution was concentrated to dryness. Methanol (4 mL) was added and the resulting solution was concentrated to dryness to afford the crude product as a light-yellow solid. Purification by silica flash chromatography (mobile phase: 30% methanol: 70% CH$_2$Cl$_2$ gradient to 50% methanol: 50% CH$_2$Cl$_2$) afforded pure cHPMPU in 69% yield as a white amorphous solid. $^1$H NMR (300 MHz, D$_2$O) d 7.62 d (1H, J=7.1 Hz, CH=CH), 5.82 d (1H, J=7.8 Hz, CH=CH), 4.30-3.71 m (7H, CH$_2$CH(OCH$_2$P)CH$_2$OH), NH and OH not observed in D$_2$O. $^{13}$C NMR (75 MHz, D$_2$O) d, 169.6 s (4-C), 155.1 s (2-C), 150.4 s (6-C), 104.2 s (5-C), 76.71 d (J$_{P,C}$=3.6 Hz, 2'—CH$_2$), 72.30 d (J$_{P,C}$=6.2 Hz, 3'—CH$_2$), 67.90 d (J$_{P,C}$=142.0 Hz, P—CH$_2$), 50.71 s (1'—C). $^{31}$P NMR (121 MHz, D$_2$O) d 9.23 s.

EXAMPLE 10

HPMPC ethyl ester

To a stirred solution of diethyl HPMPC (1.1g) in DMF, NaH (115 mg) was added. After 15 min, the reaction mixture was quenched with acetic acid (1 eq). The solvents were removed under reduced pressure. The crude mixture was dissolved in CH$_2$Cl$_2$ and water. The organic layer was washed with NaCl solution and the crude material obtained was purified on a silica gel column (elution with 5%–10% MeOH in CH$_2$Cl$_2$) to get cyclic ethyl HPMPC (950 mg) as a diastereomeric mixture (approximately 70%).

EXAMPLE 11 cHPMPC esters

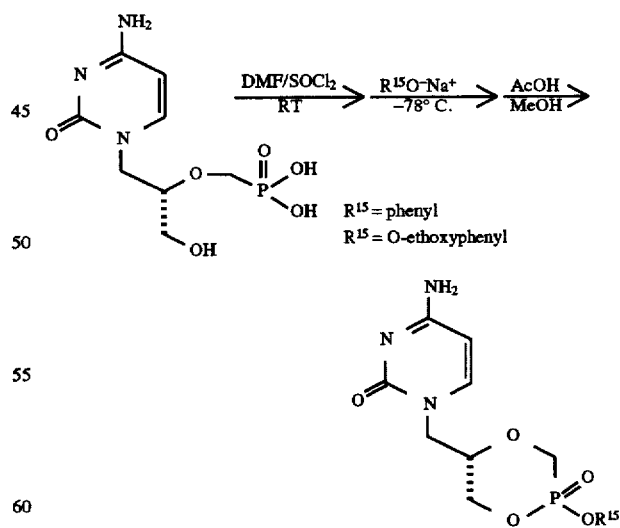

To a stirred suspension of HPMPC (2.79 g) in DMF, thionylchloride (2.1 mL) was added dropwise under anhydrous conditions and the mixture was stirred for 1 hr. In another flask, sodium aryloxide (using the appropriate aryl substituent) was made using the corresponding phenol (8.9 g) and NaH (1.8 g) in 1:1 DMF/THF (50 mL). This solution was cooled to −78° C. and the chloridate solution was added dropwise under anhydrous conditions. After 2 hrs, the reaction mixture was quenched with acetic acid (5 eq) and the solvents were evaporated under vacuum. The crude mixture was partitioned between water and $CH_2Cl_2$. The organic layer was concentrated and the residue was purified on a silica gel column (elution with 5%–10% MeOH in $CH_2Cl_2$) to get the cyclic aryl compound as a single diastereomer in approximately 60% yield. This method is suitable for all substituted or unsubstituted $R^{15}$ groups, especially aryl, subject of course to conventional protection of labile groups other than amino for which reaction is undesired (amino is protected by reaction with DMF and deprotected with acetic acid and alkanol treatment). This method offers the advantages of producing substantially stereochemically pure product, superior yield and ease of synthesis.

EXAMPLE 12 cHPMPC esters

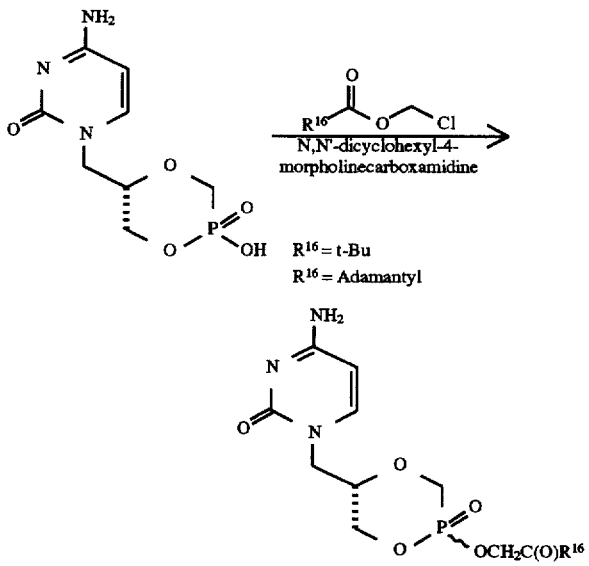

To a stirred suspension of cyclic HPMPC (1 mmol) was added N,N'-dicyclohexyl-4-morpholinecarboxamidine (2 mmol) followed by the corresponding acyloxymethyl chloride (1.5 mmol). The reaction was stirred for 3 days and the DMF was evaporated under reduced pressure. The crude was purified on a silica gel column (eluted with 5% methanol in methylene chloride) to get the pure cyclic HPMPC derivatives (approximately 30% yield).

The final product was obtained in higher yield by the same reaction using cyclic H:PMPC (1 mmol), N,N'-dicyclohexyl-4-morpholine-carboxamidine (1.1 mmol) followed by the corresponding acyloxymethyl chloride (1.2 mmol). $N^4$-benzoyl cHPMPC pivaloyloxymethyl ester was synthesized in a similar manner using $N^4$-benzoyl cHPMPC as the starting material

EXAMPLE 13 cHPMPC esters cHPMPC esters were synthesized using appropriate reactants essentially as described in Example 11 for ester moieties corresponding to structure numbers 6, 7, 11, 12, 13, 23, 24, 25 and 26 in Table 3. cHPMPC esters were synthesized using approrpiate reactants essentially as described in Example 12 for ester moieties corresponding to structure numbers 8, 9, 10, 16 and 17 in Table 3. Melting point data for cHPMPC esters of compound numbers 6, 8, 9, 11, 24, 25 and 26 was as follows: cHPMPC 3-pyridyl ester (#6)—268°–273° C. (decomposes); cHPMPC N-ethylmorpholino ester (#7)—241° C.; cHPMPC —$CH_2$—O—C(O)—$C_6H_5$ ester (#8)—198°–201° C; cHPMPC #9 ortho ester #176° C.; cHPMPC #11 ester—100–250° C. (decomposes); cHPMPC phenyl ester (#12) —190° C.; cHPMPC #24 ester—218°–225° C. (waxy liquid); cHPMPC #25 ester—171° C.; cHPMPC #26 ester—181° C.

EXAMPLE 14

9-[2,3-dideoxy-2,3-didehydro-4-phosphonomethoxy-β-D-erythrofuranosyl]adenine esters Compounds were synthesized by addition-elimination reaction using

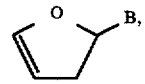

where B was adenine with iodine (2 equivalents) in acetonitrile and a compound having the structure $(R^{15}O)_2P(O)$—$CH_2$—OH (where $R^{15}$ was isopropyl, phenyl or 2-ethoxyphenyl) to yield the 3-iodophosphonate

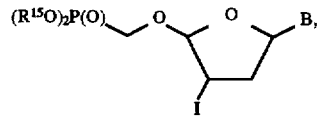

which was then eliminated to yield the corresponding structure V compound by reaction with 5 equivalents of sodium methoxide or DBU in anhydrous organic solvent such as methanol or tetrahydrofuran at room temperature for 12 hours.

Compounds of structure $(R^{15}O)_2P(O)$—$CH_2$—OH where $R^{15}$ was phenyl or 2-ethoxyphenyl were obtained by reaction of 1 equivalent of $PCl_3$ with 1 equivalent of t-butanol at 55° C. to obtain $(R^{15}O)_2P(O)H$ (U.S. Pat. No. 3,329,742). $(R^{15}O)_2P(O)H$ was then silylated using 1 equivalent of bis(trimethylsilyl)-trifluoroacetamide and the resulting $(R^{15}O)_2P(OTMS)$ was dried under vacuum. $(R^{15}O)_2P(OTMS)$ was then converted to $(R^{15})_2P(O)$—$CH_2$—OH by reaction in paraformaldehyde containing catalytic amounts of titanium isopropoxide (or another lewis acid such as titanium tetrachloride and the like can be used) for 12 hrs (12–16 hours) at 70° C. (65° to 75° C.). The 2-ethoxyphenyl product was isolated by crystallization. The bis-phenyl product was isolated by silica gel chromatography.

bis(2-ethoxyphenyl) D4AMPI ester: $^1$H-NMR (300 MHz, $CDCL_3$) δ8.38 (s, 1H), 7.97 (s, 1H), 7.21–6.82 (m, 9H), 6.40 (d, 1H, J=5.7 Hz), 6.30 (d, 1H, J=5.8 Hz), 6.16 (s, 1H), 5.61 (s, 2H), 4.48 (dd, 1H, J=14, 8.8 Hz), 4.38 (dd, 1H, J=14, 6.5 Hz, 4.10–3.93 (m, 4H), 1.38 (t, 3H, J=7.1 Hz), 1.35 (t, 3H, J=7.1 Hz); $^{31}$P-NMR (121 MHz, $CDCL_3$)δ14.6.

bis(phenyl) D4AMPI ester: $^1$H-NMR (300 MHz, $CDCL_3$) δ8.38 (s, 1H), 7.93 (s, 1H), 7.34–7.10 (m, 10H), 7.03 (s, 1H), 6.42 (d, 1H, J=5.6 Hz), 6.34 (d, 1H, J=5.6 Hz), 598 (s, 1H), 5.83 (s, 2H), 4.32 (dd, 1H, J=14, 6.5 Hz), 4.19 (dd, 1H, J=14, 6.5 Hz); $^{31}$P -NMR (121 MHz, $CDCL_3$) δ13.3.

$(C_6H_4(OC_2H_5)$—$O)_2P(O)$—$CH_2$—OH: $^1$H-NMR (300 MHz, $CDCL_3$) δ7.36–7.16 (m, 10H), 4.19 (dd, 2H, J=6.7, 5.9 Hz), OH not detected; $^{31}$P -NMR (121 MHz, $CDCL_3$) δ17.0.

($C_6H_5$—O)$_2$P(O)—CH$_2$—OH: $^1$H-NMR (300 MHz, CDCL$_3$) δ7.25–6.89 (m, 8H), 4.24 (d, 2H, J=5.01 Hz), 4.18–4.08 (m, 4H), 1.46 (t, 6H, J=7.0 Hz); $^{31}$P-NMR (121 MHZ, CDCL$_3$) δ19.9.

EXAMPLE 15

N$^4$-benzoyl cHPMPC

The title compound was synthesized using N$^4$-benzoyl HPMPC diethyl ester tritylated at the hydroxyl group as a starting material. The starting material was detritylated using acetic acid and then converted to N$^4$-benzoyl HPMPC using TMSBr. The resulting compound was converted to N$^4$-benzoyl cHPMPC using DCC and morpholine in pyridine. The title compound was tested for activity against HCMV in tissue culture (NHDF cell line) and was found to be active with an IC$_{50}$ of 22 µM compared with 0.4 µM for HPMPC.

$^1$HNMR (300 MHz, CDCL$_3$) δ8.02 (H$_6$, $_1$H, d, 7.2 Hz), 7.97 (aromatic, 2H, d, 7.2 Hz), 7.62 (aromatic, 1H, t, 7.2 Hz), 7.5 (aromatic, 2H, t, 7.2 Hz), 7.26 (H$_5$, 1H, d.7.2 Hz), 4.28 (1H, t, 14.7 Hz), 4.15 (1H, t, 10.8 Hz), 4.0 (m, 3H), 3.84(1H, m), 2.49 (1H, d, 14.1 Hz); $^{31}$P-NMR (121 MHz, CDCL$_3$) δ10.07. Melting point 243°–246° C.

EXAMPLE 16 cHPMPC esters

We synthesized formula (1) cHPMPC esters by one of three methods. In the first method, "method A", we added HPMPC (6.74 g, 0.024 mol) to a stirred suspension of Viismeier reagent (7.7 g, 0.060 mol) in CH$_3$CN (250 mL) and continued stirring the reaction mixture for three hours. We then added a solution of a formula (6) sodium salicylate (0.120 mol; freshly made from the corresponding salicylate and NaH in DMF or in a DMF-tetrahydrofuran (THF) 1:1 (v/v) mixture) to the chloridate reaction mixture at once.

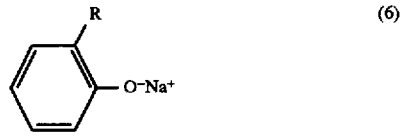

(6)

After 2 hours, the solids were filtered off. The solids were washed with 100 mL CH$_3$CN and then washed with 100 mL CH$_2$Cl$_2$. The combined flitrates were concentrated under reduced pressure. The crude residue was dissolved in 50 mL CH$_2$Cl$_2$ and this was slowly added to 500 mL of diethyl ether with stirring. The solid was collected by filtration and was identified by $^1$H NMR and $^{31}$P NMR as about 90% of the equitorial isomer and about 10% of the axial isomer (at the phosphorus atom) of cHPMPC salicylate ester (~50–60%), i.e., a formula (1) compound where all R$^1$ were hydrogen and R was not hydrogen.

We converted the equatorial isomer to the axial isomer as follows. We dissolved cHPMPC salicylate ester (equitorial isomer, 3.3 g, 6.7 mmol) in 30 mL of a 1:1 (v/v) DMF-THF solvent mixture. We then added 7.25 mmol of the corresponding sodium salicylate in 25 mL of DMF (or in 25 mL of a DMF-THF 1:1 mixture) to the cHPMPC salicylate ester solution. The resulting solution was stirred for 16 hours at r.t. (room temperature) and then 3.8 mL of glacial acetic acid was added. The mixture was stirred for 1 hour and the solvents were removed under vacuum and the crude residue was purified by silical gel column chromatography to give predominantly the axial isomer (about 10% of the equatorial isomer and about 90% of the axial isomer at the phosphorus atom) by NMR.

We synthesized formula (1) NPEs by "method B" as follows. We slowly added oxalyl chloride (3.1 mL, 0.0357 mol) to an ice cold HPMPC suspension (4 g, 14.3 mmol) in CH$_3$CN (40 mL) and DMF (2.8 mL). We warmed the reaction mixture to room temperature and stirred it for 3 hours. A solution of formula (6) sodium salicylate (100 mmol, freshly made from NaH and the corresponding salicylic acid ester in DMF or in a DMF-THF mixture) was added to the reaction mixture and stirred overnight at room temperature. Glacial acetic acid (7.2 mL) was added to the reaction mixture and stirring was then continued for 1 hour. The reaction mixture was then concentrated under reduced pressure. The crude residue was suspended in hexane or diethyl ether or a hexane-diethyl ether mixture for 20 minutes. The solids were collected by filtration and dissolved in dioxane:1N HCl (80 mL:20 mL). The mixture was stirred for 2 hours at r.t. and the solvents were then removed under reduced pressure. The crude residue was then dissolved in 300 mL CH$_2$Cl$_2$ and washed twice with 200 mL water. The milky organic layer was dried and concentrated on a rotary evaporator. The crude product was a mixture of about 6:4 of axia(axphosphorus atom. This material was isomerized as described in method A to obtain about a 9:1 isomer ratio at the phosphorus atom, with the axial isomer as the predominant isomer.

We synthesized formula (1) NPEs by "method C" as follows. We slowly added oxalyl chloride (7.75 mL, 89.3 mmol) to an ice cold HPMPC suspension (10 g, 35.7 mmol) in CH$_3$CN (150 mL) and DMF (6.9 mL). We warmed the reaction mixture to room temperature and stirred it for 3 hours. A solution of formula (6) sodium salicylate (178.6 mmol, freshly made from NaH and the corresponding salicylic acid ester in THF or DMF or in a DMF-THF mixture) was slowly added to the reaction mixture over a 30 minute period and the mixture was then stirred for 3 hours at r.t. and the solvents were then removed under reduced pressure. The crude residue was then dissolved in 300 mL CH$_2$Cl$_2$ and washed twice with 100 mL water. The organic layer was dried and concentrated on a rotary evaporator. The crude product was subjected to silica gel chromatography to obtain the salicylate ester of cHPMPC, i.e., the formula (1) compound, in about a 9:1 isomer ratio at the phosphorus atom with the equatorial isomer predominating.

The following formula (1) cHPMPC compounds were synthesized—all R$^1$ were hydrogen and R is as designated. The desigantion (eq) means the equatorial isomer at the phosphorus atom was present in about a 9:1 ratio over the axial isomer. The desigantion (ax) means the axial isomer at the phosphorus atom was present in about a 9:1 ratio over the equatorial isomer.

| R | method |
|---|---|
| —COO(CH$_2$)$_3$CH$_3$ (eq) | A, C |
| —COO(CH$_2$)$_3$CH$_3$ (ax) | A, B |
| —COO(CH$_2$)$_4$CH$_3$ (ax) | B |
| —COO(CH$_2$)$_5$CH$_3$ (eq) | A |
| —COO(CH$_2$)$_5$CH$_3$ (ax) | A, B |
| —COO(CH$_2$)$_9$CH$_3$ (ax) | A |
| —COOCH[(CH$_2$)$_2$CH$_3$]2 (ax) | A |
| —COOCH$_2$CH(C$_2$H$_5$)(CH$_2$)$_3$CH$_3$ (eq) | A |
| —COOCH$_2$CH(C$_2$H$_5$)(CH$_2$)$_3$CH$_3$ (ax) | A |
| —COOC$_6$H$_{11}$ (ax) | A |
| —COOC$_6$H$_5$ (eq) | A |
| —COOC$_6$H$_5$ (ax) | A |
| —COOC$_6$H$_4$-p-(CH$_3$)$_3$ (eq) | A |
| —COOC$_6$H$_4$-p-(CH$_3$)$_3$ (ax) | A |
| —COOCH$_2$C$_6$H$_5$ (ax) | A |

| R | method |
|---|---|
| —COOCH$_2$CH$_2$C$_6$H$_5$ (eq) | A |
| —COOCH$_2$CH$_2$C$_6$H$_5$ (ax) | A,B |

We obtained the following NMR spectra for the indicated formula (1) compounds (all R$^1$ were hydrogen).

R=—C(O)OCH$_2$CH$_2$C$_6$H$_5$ (equitorial isomer) $^1$H NMR (300 MHz, CDCl$_3$): δ7.85 (1H, d, J=7.5 Hz), 7.5 (1H, t, J=7.8 Hz), 7.35–7.2 (8H, m), 5.75 (1H, d, J=7.2 Hz), 4.55–4.35 (5H, m), 4.2–4.1 (2H, m), 4.05 (1H, d, J=14.4 Hz), 3.56 (1H, dd, J$_1$=15 Hz, J$_2$=8.1 Hz), 3.0 (2H, t, J=6.9 Hz).

R=—C(O)OCH$_2$CH$_2$C$_6$H$_5$ (axial isomer) $^1$H NMR (300 MHz, CDCl$_3$): δ7.84 (1H, d, J=7.8 Hz), 7.55–7.2 (9H, m), 5.64 (1H, d, J=7.2 Hz), 4.55 (1H, t, J=10 Hz), 4.50 (2H, t, J=6.9 Hz), 4.5–4.3 (2H, m), 4.15–4.1 (2H, m), 4.0 (1H, dd, J$_1$=14.7 Hz, J$_2$=1.8 Hz), 3.52 (1H, dd, J$_1$=14.4 Hz, J$_2$=7.8 Hz), 3.0 (2H, t, J=7.2 Hz).

R=—C(O)OCH$_2$CH(C$_2$H$_5$)(CH$_2$)$_3$CH$_3$ (equatorial isomer) $^1$H NMR (300 MHz): δ7.9 (1H, d, J=7.8 Hz), 7.52 (1H, t, J=7.8 Hz), 7.45–7.2 (3H, m), 5.76 (1H, d, J=6.9 Hz), 4.6–4.4 (3H, m), 4.25–4.1 (5H, m), 3.59 (1H, dd, J$_1$=14.1, J$_2$=8.1 Hz), 1.8–1.65 (1H, m), 1.5–1.25 (8H, m), 0.98–0.85 (6H, m).

R=—C(O)OCH$_2$CH(C$_2$H$_5$)(CH$_2$)$_3$CH$_3$ (axial isomer) $^1$H NMR (300 MHz): δ7.89 (1H, d, J=7.5 Hz), 7.53 (1H, t, J=7.8 Hz), 7.42 (1H, d, J=8.1 Hz), 7.31 (1H, d, J=7.2 Hz), 7.26 (1H, t, J=7.35 Hz), 5.63 (1H, d, J=7.2 Hz), 4.65 (1H, t, J=10.8 Hz), 4.53–4.1 (2H, m), 4.25–4.1 (4H, m), 4.0 (1H, dd, J$_1$=15, J$_2$=1.2 Hz), 3.52 (1H, dd, J$_1$=13.8, J$_2$=7.5 Hz), 1.75–1.6 (1H, m), 1.5–1.2 (8H, m), 0.94 (3H, t, J=7.5 Hz), 0.917 (3H, t, J=7.2 Hz).

R=—C(O)OCH$_2$C$_6$H$_5$ (axial isomer) $^1$H NMR (300 MHz): δ7.97 (1H, d, J=7.5 Hz), 7.49 (1H, t, 7.4 Hz), 7.45–7.2 (8H, m), 5.62 (1H, d, J=7.2 Hz), 5.31 (2H, d,J=12 Hz), 4.54 (1H, t, J=10.5 Hz), 4.5–4.35 (1H, m), 4.27 (1H, dd, J$_1$=15 Hz, J$_2$=1.2 Hz), 4.15–4.05 (2H, m), 3.94 (1H, d, J=13.5 Hz), 3.42 (1H, dd, J$_1$=13.5 Hz, J$_2$=7.5 Hz).

R=—C(O)OC$_6$H$_5$ (axial isomer) $^1$H NMR (300 MHz): δ8.15 (1H, d, J=7.8 Hz), 7.6 (1H, t, 7.5 Hz), 7.65–7.2 (7H, m), 7.0 (1H, d, J=7.2 Hz), 5.56 (1H, d, J=7.2 Hz), 4.56 (1H, k, J=10.0 Hz), 4.5–4.3 (2H, m), 4.2–4.0 (2H, m), 3.95 (1H, d, J=15 Hz), 3.28 (1H, dd, J$_1$=13.8, J$_2$=7.5 Hz).

EXAMPLE 17

Oral bioavailability of cHPMPC and cHPMPC esters

This study examined the oral bioavailability of cHPMPC and cHPMPC esters in Beagle dogs. The study design obtained bioavailabilities of cHPMPC and cHPMPC esters in dogs by comparing the AUC, the area under the plasma concentration time curve, after orally administering cHPMPC or a cHPMPC ester to the AUC obtained with cHPMPC after intravenous administration.

The study used an aqueous solution of cHPMPC for oral administration containing 10 mg/mL cyclic HPMPC in 0.9% NaCl. The dose was 1.0 mL/kg (10 mg/kg). Formulations for the cHPMPC esters (10 mg/kg solutions) are described below.

The study used adult male beagle dogs. The dogs were fasted 12–18 hours before dosing and until 6 hours postdose. The average gastric pH of a fasted dog is approximately one pH unit higher than that of human and the study used pentagastrin pretreated dogs to adjust the gastric pH (J. Dressman (1986) *Pharm. Res.*, 3:123–131). Pentagastrin lowers the gastric pH to a value consistent with a fasted human subject (R. P. Happe, et al., (1982) *Research in Vet. Sci.*, 33:232–239). The study used Peptavlon (pentagastrin, 0.25 mg/mL) (Ayerst Laboratories, Inc., Philadelphia, Pa.). The dogs received a single intramuscular injection of pentagastrin (6 μg/kg) 20 minutes before dosing to simulate human gastric pH values. The dogs received water ad lib.

Each formulation was administered as a single dose. The study provided for individual vials of each formulation for each animal. The oral solutions were administered by gavage, followed by two 10 mL water washes. Animals remained conscious throughout the sample collection period.

Blood samples (4.0 mL) were collected by direct jugular vein access from each animal into heparinized tubes. Blood was processed immediately for plasma by centrifugation at 2000 rpm for 10 minutes. Plasma samples were frozen and maintained at ≦–20° C. until analyzed. Pooled normal dog plasma was used to prepare standard samples.

Plasma concentrations of cHPMPC and the tested esters were determined using reverse-phase HPLC with fluorescence detection (Excitation 305 nm, Emission 370 nm) of the fluorescent cytosine base 3,N$^4$-etheno derivative. Cytidine 5'-monophosphate (5'-CMP) (Sigma, Cat.#C-1006) was an internal standard for the HPLC analysis. Plasma (100 μL) was mixed with 400 μL of protein precipitation solution (10 mL glacial acetic acid, 190 mL water, 800 mL acetonitrile containing 5'-CMP) and the solution was then centrifuged at 20,000 g for 5 min. The supernatant was transferred to another tube and mixed with 100 μL phenacyl bromide (Fluka), 0.25 g/mL in acetonitrile to generate the cytosine etheno derivative by incubation at 65° C. for 40 min. The tubes were then put on ice to quench the reaction. The samples were then evaporated to dryness under reduced pressure for ≦2.5 hours. The residue was dissolved in 100 μL of reconstitution solution (6 mM dodecyltriethylammonium phosphate (Bodman), 30 mM phosphoric acid in water) and filtered through a 0.45 μM filtration unit (Z-spin). The filtrate was then transferred to autosampler vials (Chromacol) for HPLC analysis.

The HPLC system comprised a Model P4000 (Thermo Separations, San Jose, Calif.) solvent delivery system with a Model AS3000 autoinjector (Thermo Separations) and a Model F-1080 fluorescence detector (Hitachi). A Peak Pro data acquisition system (Beckman, Palo Alto, Calif.) acquired and stored data from the study. The column was an Intersil ODS-2, 4.6×150 mm, 5 μM HPLC column (Metachem) operated at 45° C. The mobile phase was degassed 6 mM dodecyltrietylammonium phosphate (Bodman), 30 mM phosphoric acid, pH 2.85 in 30% acetonitrile. A flow rate of 2.0 mL/min and an injection volume of 20 μL was used. HPLC grade water was used to prepare all solutions and standards for HPLC analysis.

The following formula (1) compounds were tested for oral bioavailability in the same manner as that used for cHPMPC measurements. The tested esters all consisted of about a 90:10 (w/w) racemic mixture at the phosphorus atom and for all compounds, the same isomer predominated.

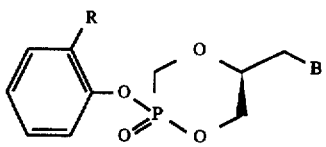

(1)

| Compound # | formulation # | R |
|---|---|---|
| 1 (cHPMPC) | 1 | none |
| 2 | 2 | —COOCH$_2$CH$_3$ |
| 3 | 3 | —COOCH$_2$CH$_2$CH$_2$CH$_3$ |
| 4 | 3 | —COOCH$_2$CH$_2$CH$_2$CH$_2$CH$_3$ |
| 5 | 3 | —COOCH$_2$CH(CH$_2$CH$_3$)CH$_2$CH$_2$CH$_2$CH$_3$ |
| 6 | 2 | —COOC$_6$H$_5$ |
| 7 | 3 | —COOC$_6$H$_{11}$ |
| 8 | 3 | —COOCH$_2$CH$_2$C$_6$H$_5$ |

The R group in compound #7 was cyclohexyl and the R group in compound #8 was phenethyl. The formulations that were used to deliver cHPMPC compounds consisted of the following: Formulation #1 0.9% NaCl, #2 PEG 400, #3 20% PEG 400 and 80% aqueous citric acid buffer (50 mM, pH 2.2). The compounds were orally bioavailable as cHPMPC follows: Compound #1, 22.5%±11.0; compound #2, 18.5%±5.8; compound #3, 46.3%±9.0; compound #4, 30.5%±4.8; compound #5, 34.4%±4.8; compound #6, 27.8%±6.2; compound #7, 22.7%±4.4; compound #8, 35.3%±3.4. Bioavailability of the compounds as HPMPC ranged from 12.0%±2.6 to 1.4%±1.2, with the latter value coming from cHPMPC.

We claim:

1. A compound having the structure of formula (1)

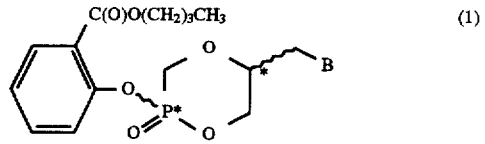

(1)

or a salt, solvate or racemate thereof wherein B is a protected or unprotected heterocyclic cytosin-1-yl.

* * * * *